United States Patent [19]
Caetano-Anollés

[11] Patent Number: 5,962,221
[45] Date of Patent: *Oct. 5, 1999

[54] OLIGONUCLEOTIDE CONSTRUCTS AND METHODS FOR THE GENERATION OF SEQUENCE SIGNATURES FROM NUCLEIC ACIDS

[76] Inventor: Gustavo Caetano-Anollés, 1320 Beacon Hill La., Knoxville, Tenn. 37919

[*] Notice: This patent is subject to a terminal disclaimer.

[21] Appl. No.: 08/489,269

[22] Filed: Jun. 9, 1995

Related U.S. Application Data

[63] Continuation-in-part of application No. 08/139,459, Oct. 20, 1993, which is a continuation-in-part of application No. 08/006,380, Jan. 19, 1993, Pat. No. 5,413,909.

[51] Int. Cl.⁶ ............... C12Q 1/68; C07K 21/04
[52] U.S. Cl. ........... 435/6; 435/91.1; 435/91.2; 435/810; 536/22.1; 536/23.1; 536/24.1; 536/24.3; 536/24.31; 536/24.32; 536/24.33; 935/77; 935/78
[58] Field of Search ................ 435/5, 6, 91.1, 435/91.2, 810; 536/22.1, 23.1, 24.1, 24.3–24.33; 935/77, 78

[56] References Cited

U.S. PATENT DOCUMENTS

| | | | |
|---|---|---|---|
| 5,002,867 | 3/1991 | Macevicz | 435/6 |
| 5,043,272 | 8/1991 | Hartley | 435/91 |
| 5,487,985 | 1/1996 | McClelland et al. | 435/91.2 |

FOREIGN PATENT DOCUMENTS

| | | |
|---|---|---|
| WO 91/14001 | 9/1991 | WIPO . |
| WO 92/07095 | 4/1995 | WIPO . |

OTHER PUBLICATIONS

Kleppe et al. (1971) J. Mol. Biol., vol. 56, pp. 341–361.

Caetano–Anollés, G. and Gresshoff, P. M., "DNA Amplification Fingerprinting Using Arbitrary Mini–Hairpin Oligonucleotide Primers", Bio/Technology, 12:619–623 (1994).

Zietkiewicz, E., Rafalski, A., and Labuda, D., "Genome Fingerprinting by Simple Sequence Repeat (SSR)–Anchored Polymerase Chain Reaction Amplification", Genomics, 20:176–183 (1994).

Wu, K., Jones, R., Danneberger, L., and Scolnik, P. A., "Detection of Microsatellite Polymorphisms Without Cloning", Nucleic Acids Research, vol. 22, No. 15, pp. 3257–3258 (1994).

Lamture, J.B., Beattie, K.L., Burke, B.E., Eggers, M.D., Ehrlich, D.J., Fowler, R., Hollis, M.A., Kosicki, B.B., Riech, R.K., Smith, S.R., Varma, R.S., and Hogan, M.E., "Direct Detection of Nucleic Acid Hybridization on the Surface of a Charge Coupled Device", Nucleic Acids Research, vol. 22, No. 11, pp. 2121–2125 (1994).

Caetano–Anollés, G. and Gresshoff, P. M., "DNA Amplification Fingerprinting of Plant Genomes" Method in Molecular and Cellular Biology, 5:62–70 (1994).

Caetano–Anolles, Bassam and Gresshoff, "Primer–template interactions during DNA amplification fingerprinting with single arbitrary oligonucleotides", vol. 235, Molecular & General Genetics, (1992) pp. 157–165.

Caetano–Anolles, Bassam and Gresshoff, "Enhanced detection of polymorphic DNA by multiple arbitrary amplicon profiling of endonuclease–digested DNA: identification of markers tightly linked to the supernodulation locus in soybean", vol. 241, Molecular & General Genetics (1993) pp. 57–64.

Primary Examiner—Ardin H. Marschel

[57] ABSTRACT

Novel oligonucleotides for amplification and profiling of nucleic acid templates are disclosed. Enhancements of nucleic acid fingerprinting methods are disclosed.

39 Claims, 11 Drawing Sheets

OLIGONUCLEOTIDE CONSTRUCTS AND METHODS FOR THE GENERATION OF SEQUENCE SIGNATURES FROM NUCLEIC ACIDS

RELATED PATENT APPLICATIONS

This application is a continuation-in-part application of pending application Ser. No. 08/139,459 (the "second parent application"), filed Oct. 20, 1993, which is in turn a continuation-in-part application of application Ser. No. 08/006,380, (the "first parent application") filed Jan. 19, 1993 entitled "DNA Amplification Fingerprinting", which issued as U.S. Pat. No. 5,413,909 on May 9, 1995. Both parent applications are incorporated herein by reference.

FIELD OF THE INVENTION

The invention relates to "fingerprinting of nucleic acids", that is, generating a signature characteristic of the base sequence of a nucleic acid template.

BACKGROUND OF THE INVENTION

A novel method for the fingerprinting of nucleic acids that uses at least one oligonucleotide to prime arbitrary segments of a nucleic acid template to produce a characteristic set of amplified fragments is being shown to be of increasing value in the analysis of genetic relationships. Fingerprint complexity varies from very simple, and thus ideal for genome mapping, to highly complex and more suitable for fingerprinting applications. See Bio/Technology, Vol. 10:937, September 1992, incorporated herein by reference.

DNA amplification fingerprinting (DAF) is the enzymatic amplification of arbitrary stretches of at least one nucleic acid which is directed by short oligonucleotide primers of arbitrary sequence to generate complex but characteristic DNA fingerprints.

The amplification mechanism proposed by the inventors can be seen in Amplifying DNA with Arbitrary Oligonucleotide Primers, Review 1993, Cold Spring Harbor Laboratory Press which is incorporated herein by reference and attached hereto. Of particular interest is the description of the step by step amplification described at pages 2 and 3.

Terms and terminology used in conjunction with the invention are known in the art. For instance, "oligonucleotide", "primer", "restriction endonuclease" and "restriction enzymes", "DNA polymorphism", "Restriction fragment, length polymorphism", ("RFLP"), "random nucleic acid fragment", "DNA fingerprinting", or "DNA typing", "genotyping", "profiling", "DNA identification analysis", or "DNA polymorphism", "polymerase chain reaction" ("PCR"), "DNA amplification", "random amplified polymorphic DNA" ("RAPD"), "amplicons", "arbitrary primer", "specific primer", "degenerate base", "degenerate primer", "sequence tagged site" ("STS"), "sequence characterized amplified region" ("SCAR"), and "DNA amplification fingerprinting" ("DAF") are discussed in the patent and other scientific literature, such as in the U.S. Pat. Nos. 4,683,202 (Mullis), 5,126,239 (Livak et al.), PCT Publication No. WO 92/03567 Caetano-Anolles et al., which are incorporated herein by reference. For "Genomes" ("complex and simpler", see Genes IV by Benjamin Lewin, Chapter 24 (1990), ranging from as little as $10^6$ for a mycoplasma to as much as $10^{11}$ bp for some plants and amphibians, which is incorporated herein by reference.

SUMMARY OF THE INVENTION

Figure 1A:
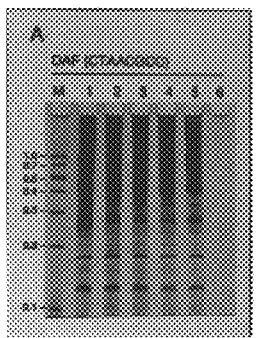
FIG. 1A & B & C show reamplification and bulked segregant analysis of the supernodulation nts locus by ASAP analysis.

This application discloses methods of optimization of the use of arbitrary primers for the fingerprinting of nucleic acid, including DAF technology, so as to maximize the detection and visualization of polymorphisms of a nucleic acid template. The optimization is achieved by modification of the methodology and/or by the use of new oligonucleotide primers.

In one embodiment of the invention, products obtained by amplification of a nucleic acid template are reamplified one or more times with one or more primers. Subsequently, the characteristic pattern of the fragments produced by the reamplification is determined. The template can be of any known or unknown DNA or RNA sequence, including, for example, bacteria, plants, animals, subgenomic DNA such as mitochondrial DNA and PCR products, and cloned nucleic acids in suitable vectors, such as phages, plasmids, bacterial artificial chromosomes (BAC), mammalian artificial chromosomes (MAC), and yeast artificial chromosomes (YAC).

Any primer can be used for the initial amplification. The primer can be an arbitrary unstructured primer, such as a DAF primer of at least 5 nucleotides in length, typically 5 to 25 nucleotides in length, a hemiarbitrary primer, such as a mini-hairpin primer, or a non-arbitrary primer, preferably of at least 5 nucleotides in length, such as any specific unstructured PCR primer. The primer may be an SSR primer, described in detail below. The primer can also include degenerate bases in its sequence, such as hypoxanthine substitutions or A, G, C, and T in a particular location of the sequence. The amount of primer, in mass, is preferably in excess of the amount of template for both the initial and subsequent amplifications. Subsequent amplifications are with a primer, which may be any of the primers described above for the initial amplification, and which may be the same primer or a different primer than that used for the initial amplification.

The second, or later, amplification may be followed by the separation of the nucleic acid fragments produced in order to generate a characteristic pattern of fragments, which may be on an acrylamide gel. Such a pattern resulting from the reamplification is referred to as an Arbitrary Signature from Amplification Profile ("ASAP"). Generally, the ASAPs provide additional information and increased detection of nucleic acid sequence polymorphism than does the initial amplification.

Another embodiment of the invention is a new primer, referred to as a primer complementary to simple sequence repeats (SSR). SSR primers are oligonucleotide constructs which contain a sequence of bases complementary to microsatellite DNA. The SSR primers comprise a DNA sequence containing multiple repetitions, for example 2 to 10 repetitions, of any two, three, four, or five bases, such as AT, TA, CT, GA, CG, or GC for repetitions of two bases. The individual bases in a repetition may also be repeated, for example TATG for a repetition of 4 bases or CGACG for a repetition of 5 bases. Any sequence of bases can be the repeating sequence of the SSR primers.

A sequence of degenerate bases, of at least one nucleotide, preferably 2 to 10 nucleotides in length, is connected at the 3' or the 5' end of the sequence complementary to the microsatellite DNA. The SSR primer anneals to these microsatellite DNA segments, permitting the detection of polymorphisms based on the highly variable number of simple repeat sequences found within the microsatellite sequence. A simple SSR primer can have the following compositions: 5' (SSR sequence)(degenerate)3' or 5' (degenerate)(SSR sequence)3'.

The SSR primers may also include an arbitrary sequence ("arbitrary"), preferably of 2 to 10 nucleotides in length, attached to the sequence of degenerate bases ("degenerate") or to the sequence containing multiple repetitions ("SSR sequence"). Thus, a complex hybrid SSR primer can have the following compositions: 5'(degenerate)(arbitrary)(SSR sequence)3', 5'(degenerate)(SSR sequence)(arbitrary)3',. 5'(SSR sequence)(arbitrary)(degenerate)3', 5'(SSR sequence)(degenerate)(arbitrary)3', 5'(arbitrary)(degenerate)(SSR sequence)3', or 5'(arbitrary)(SSR sequence)(degenerate)3'.

In addition to the above, the arbitrary sequence may also be contained within the SSR sequence or the degenerate base sequence. For example (SSR sequence)(arbitrary)(SSR sequence) or (degenerate)(arbitrary)(degenerate).

The degenerate sequence of the SSR primers allows the annealing of the primer to any possible sequence in the template, whereas the arbitrary and SSR sequences of the primer are highly selective and will target defined nucleic acid regions.

A third embodiment of the invention is a method of isolation of an amplification product, for example from a silver-stained polyacrylamide gel, and the reamplification of the amplification product as a source of template for further amplification. This method allows for increased detection of polymorphisms between closely related species.

A fourth embodiment of the invention is the modification of the DAF technology to increase the detection and/or visualization of polymorphisms, primarily by modifications of the separation step. An example of one such suitable modification is the real-time separation of DAF products by capillary electrophoresis ("CE"), in which, rather than the DAF products being separated on a gel, DAF products are separated in a capillary tube. Alternatively, DAF products can be subjected to Denaturing Gradient Gel Electrophoresis ("DGGE"), whereby the gel on which DAF products are electrophoresed has a pH or a temperature gradient to provide for additional means of separation of the DAF fragments. DGGE can be used in combination with CE. A third suitable technology used in conjunction with DAF to increase detection of polymorphisms is the separation of DAF products by sequence polymorphism, in contrast to separation by length polymorphism as occurs in gel electrophoresis. In one embodiment, separation of DAF products by sequence polymorphism is performed by hybridization to oligonucleotide arrays which are bound to a solid support. The solid support may be any support which will maintain the structure of the oligonucleotides of the arrays and may be a membrane or glass or magnetic beads, for example.

The DAF technology in all its manifestations, as disclosed in the parent applications and herein, is applicable to any nucleic acid template, DNA or RNA. For example, DAF is useful to detect polymorphisms in templates from viruses, bacteria, plants, animals, subgenomic DNA such as mitochondrial DNA and PCR products, and yeast artificial chromosomes. DAF can also detect sequence variations in complementary DNA (CDNA) obtained by reverse transcription from messenger RNA (mRNA).

Examples of the widespread utility of the DAF technology include the following. DAF can be used to detect differences in nucleic acid polymorphism between very closely related species or even between individuals of the same species. DAF can be used to study gene expression. DAF can be used to determine the presence of pathogenic or symbiotic organisms within a host tissue. Because DAF products are inherited, DAF can be used diagnostically to detect the presence of markers indicating the presence of a heritable disease, such as cystic fibrosis. DAF can be used to determine a genetic marker for a phenotype, for example in bulked segregant analysis, described below.

DETAILED DESCRIPTION OF THE FIGURES

Figure 1B:
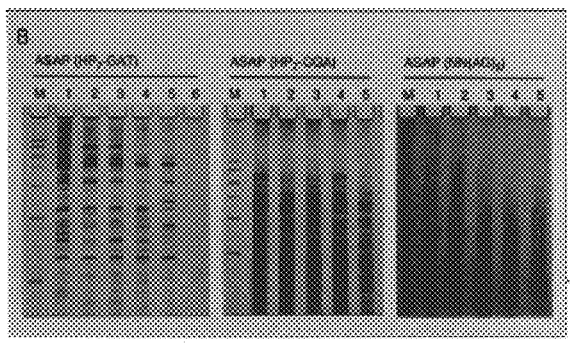
FIG. 1C shows reamplification of closely related bermudagrass cultivars.
Figure 1C:
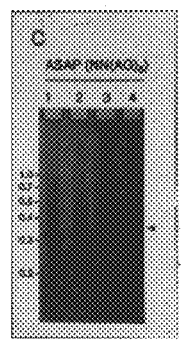

FIGS. 1A and B show bulked segregant analysis of the supernodulation nts locus by ASAP analysis. Pools of soybean DNA from wild type (lane 4) and supernodulating (lane 5) $F_2$ segregants, and controls that include the parents *Glycine soja* accession PI468.387 (lane 1) and soybean (*Glycine max*) mutant nts382 (lane 3), wild-type soybean cultivar Bragg (lane 2), and no template (lane 6) were amplified with primer CTAACGCC (FIG. 1A) and then re-amplified with mini-hairpin primers ($HP_7$-GAT and $HP_7$-CGA; $HP_7$=GCGAAGC) or an SSR degenerate primer ($NN(AG)_6$, where N is A, T, G, or C) (FIG. 1B). Polymorphic bands differentiate the bulked DNA. FIG. 1C shows ASAP analysis of closely related bermudagrass (*Cynodon dactylon* X *Cynodon transvaalensis*) cultivars Tifway (lane 1), Tifway II (lane 2), Tifgreen (lane 3) and Tifdwarf (lane 4) originally amplified with CCTGTGAG, and subsequently reamplified with $NN(AG)_6$. The arrow indicates a diagnostic co-dominant marker. Molecular weight standards (M) are given in kb.

Figure 2A:
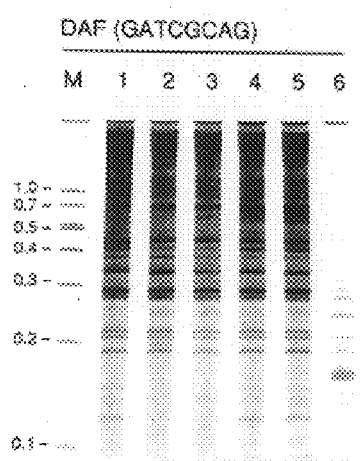
FIG. 2A & B shows bulked segregant analysis of the supernodulation nts locus of soybean by ASAP analysis. Initial amplification was with an unstructured octamer primer which was followed by reamplification with a different unstructured octamer primer.
Figure 2B:
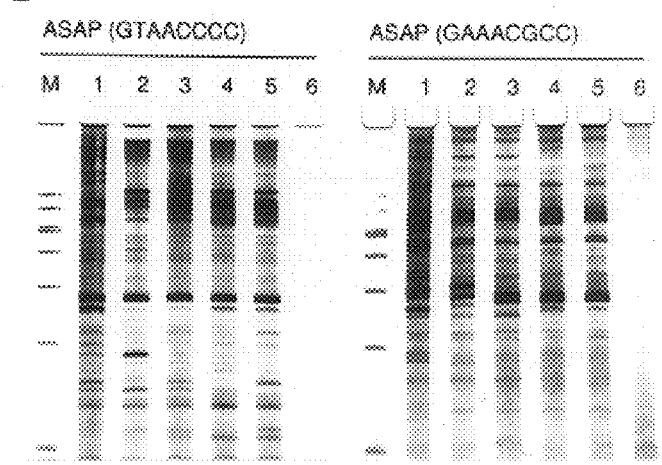

FIG. 2 shows bulked segregant analysis of the supernodulation nts locus by ASAP analysis. Pools of soybean DNA from wild type (lane 4) and supernodulating (lane 5) $F_2$ segregants, and controls that include the parents *Glycine soja* accession PI468.387 (lane 1) and soybean (*Glycine max*) mutant nts382 (lane 3), wild-type soybean cultivar Bragg (lane 2), and no template (lane 6) were amplified with primer GATCGCAG (FIG. 2A) and then reamplified with octamers GTAACCCC or GAAACGCC (FIG. 2B). Molecular weights standards (M) are given in kb.

Figure 3A:
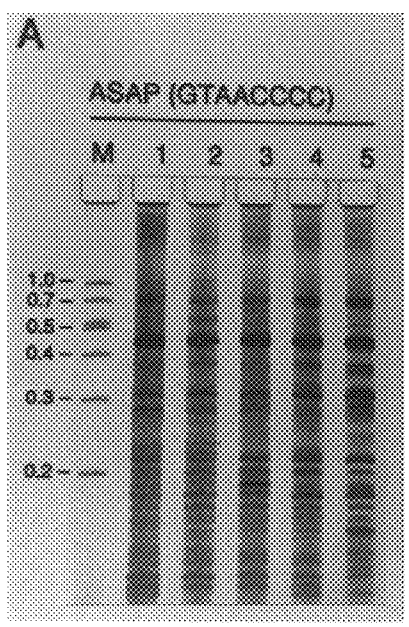
FIG. 3A & B shows bulked segregant analysis of the supernodulation nts locus of soybean by ASAP analysis. Initial amplification was with an unstructured octamer primer which was followed by reamplification with a mini-hairpin decamer primer.
Figure 3B:
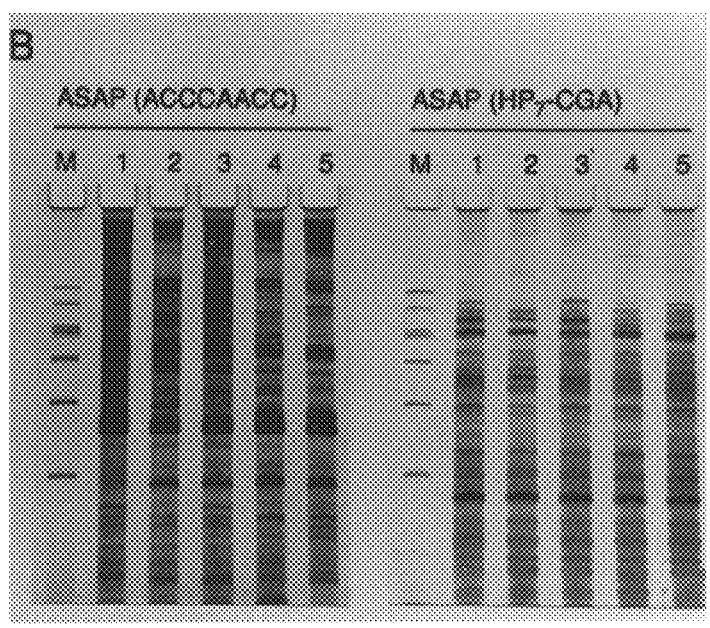

FIG. 3 shows bulked segregant analysis of the supernodulation nts locus by ASAP analysis. Pools of soybean DNA from wild type (lane 4) and supernodulating (lane 5) $F_2$ segregants, and controls that include the parents *Glycine soja* accession PI468.387 (lane 1) and soybean (*Glycine max*) mutant nts382 (lane 3), wild-type soybean cultivar Bragg (lane 2), and no template (lane 6) were amplified with primer GTAACCCC and then reamplified with octamer GTAACCCC (FIG. 3A) or were amplified with primer GATCGCAG and then re-amplified with either ACCCAACC or $HP_7$-CGA (FIG. 3B). Molecular weights standards (M) are given in kb.

Figure 4:
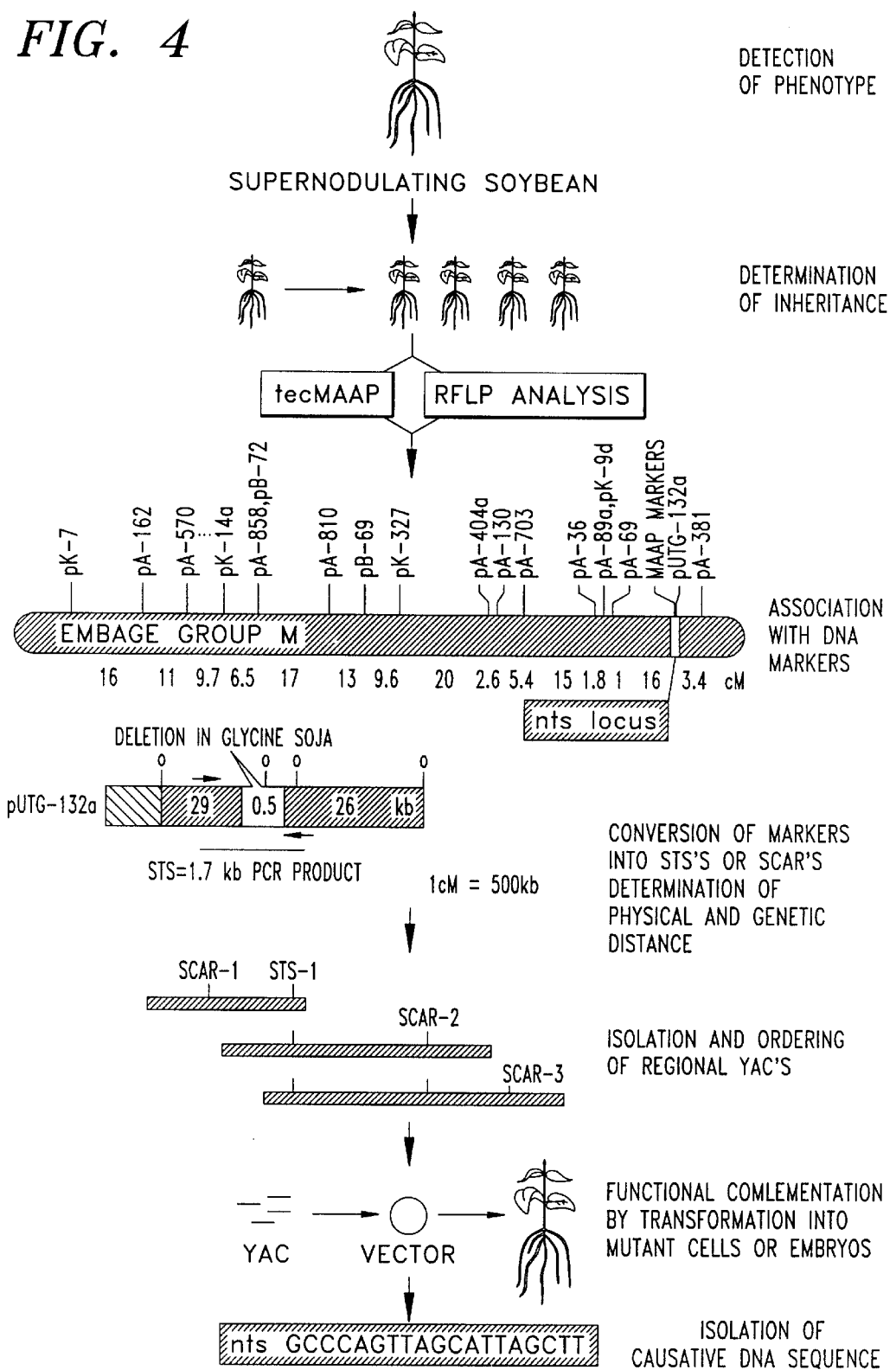
FIG. 4 shows the steps in positional cloning of a gene.

FIG. 4 shows steps in the positional cloning of a plant gene. Small arrows indicate position of primer annealing sites. Abbreviations: RFLP, restriction fragment length polymorphism; tecMAAP, template endonuclease digested MAAP; STS, sequence-tagged sites; SCAR, sequence-characterized amplified region; YAC, yeast artificial chromosome.

Figure 5:
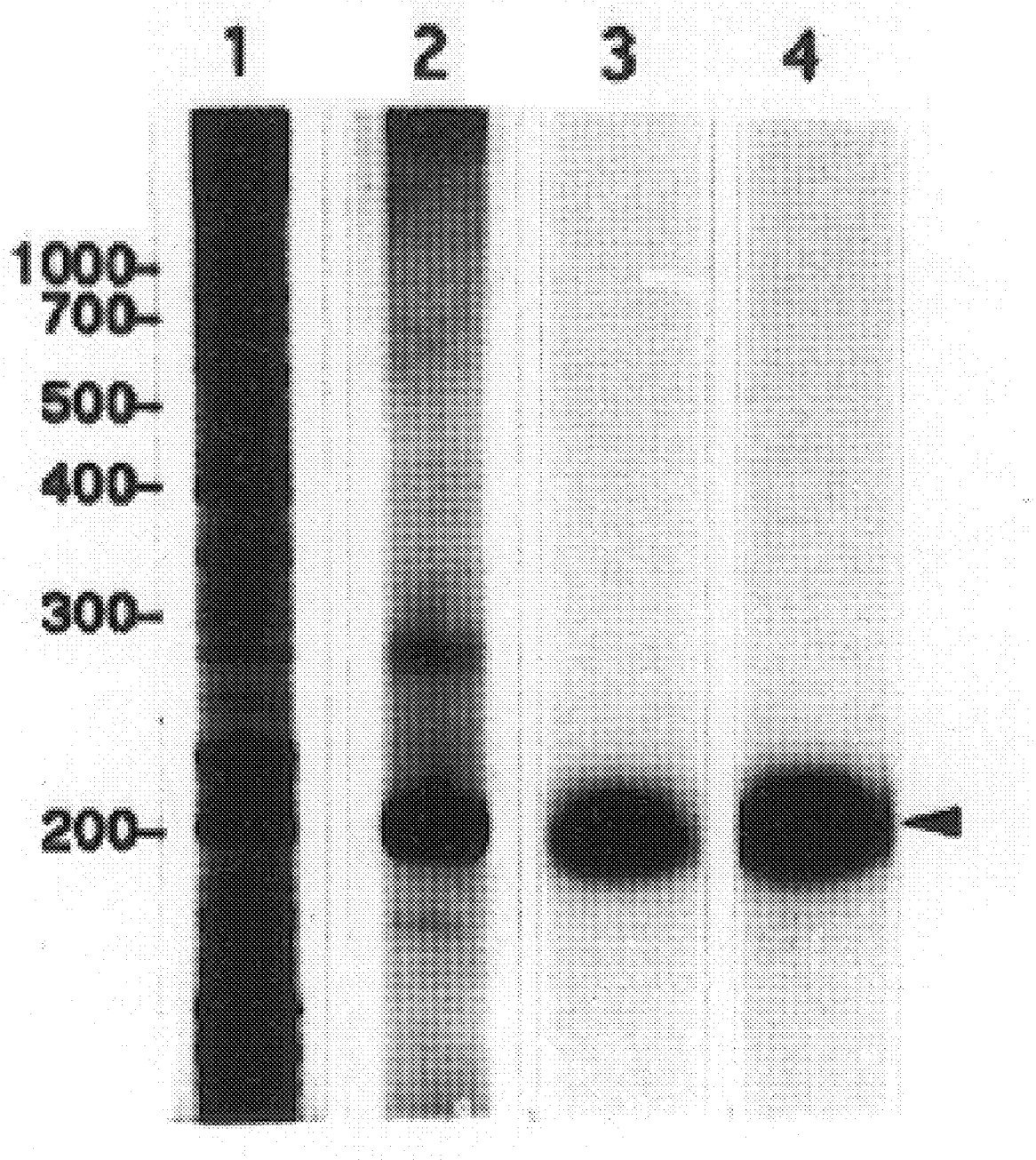
FIG. 5 shows the isolation of a 200-bp DNA fragment from centipedegrass DNA amplified with an unstructured primer.

FIG. 5 shows isolation of 200-bp DNA fragment from centipedegrass DNA amplified with an arbitrary octamer primer. A monomorphic fragment (arrowhead) was isolated from a DNA profile obtained from *Eremochloa ophiuroides* (Munro) Hack. cv. "Tennessee Hardy" by DAF using primer AACGGGTG (5'–3'). This fragment was present in four other centipedegrass cultivars. Lane 1, DAF profile; lane 2, isolated DNA fragment; lanes 3 and 4, confirmation of isolation by Southern hybridization of the isolated 200-bp fragment to the profile of lane 1 transferred to a nylon membrane. In lane 3 the blot was probed with a subcloned isolated fragment. The DAF product was ligated into the vector PCRII (Invitrogen, San Diego, Calif., USA) following directions of the manufacturer. Inserts were amplified by the PCR and cloned fragments labeled for hybridization by amplification with [$\alpha$-$^{32}$P] ATP (8).

Figure 6:
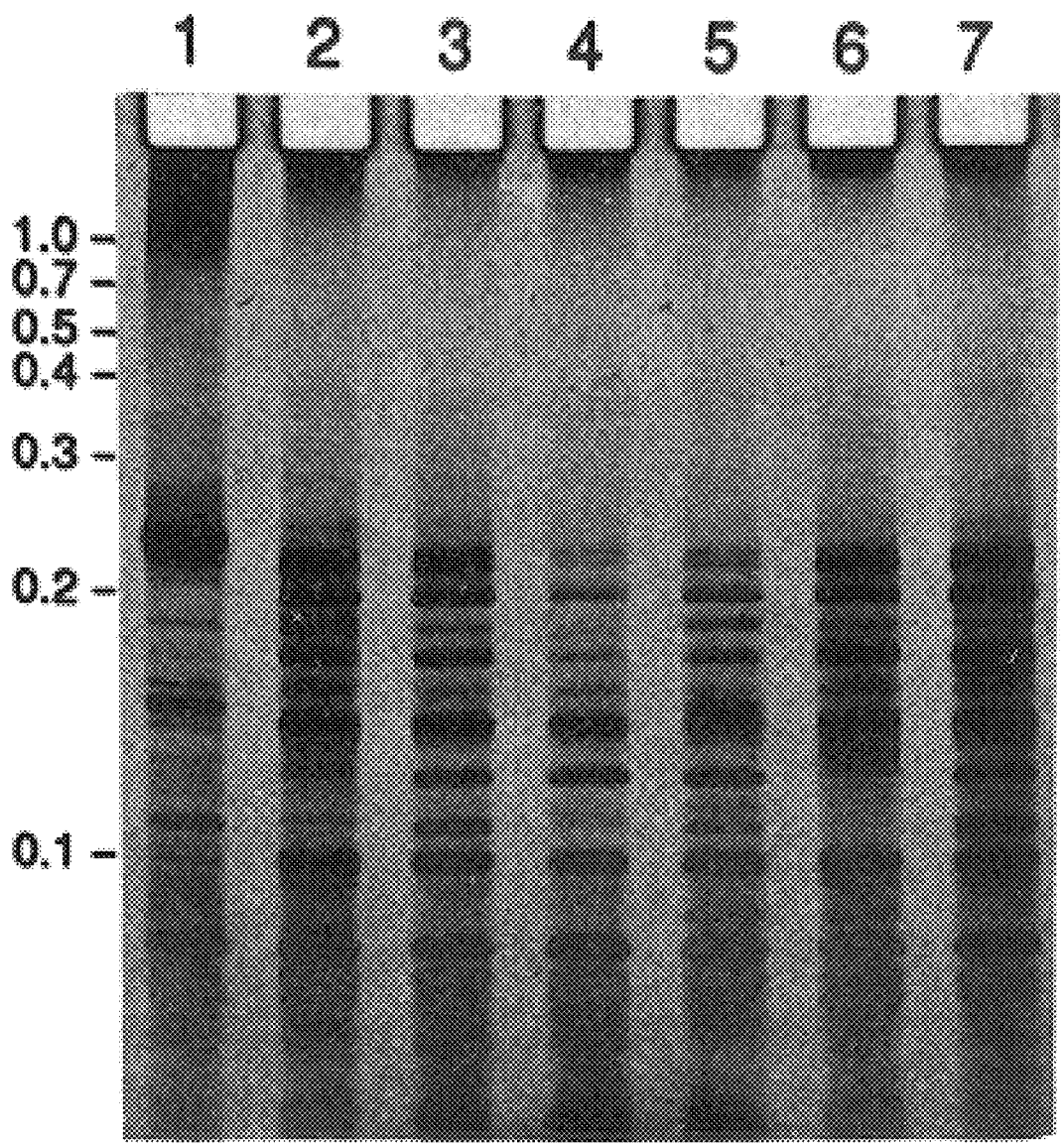
FIG. 6 shows fingerprints obtained when amplifying YACs containing cloned soybean DNA.

FIG. 6 shows fingerprinting of a low complexity template DNA. DNA amplification of several clones from a soybean YAC library was amplified using the mini-hairpin primer GCGAAGC-CTG. YAC64 (lane 2), YACS8 (lane 3), YACS4 (lane 4), YAC7 (lane 5) and YACU9 (lane 6) contain about 100, 150, 200, 250, and 330 kb of soybean DNA, respectively, cloned in vector YAC4 (R. Funke, unpublished). As a control, AB1380 (lane 7) contains no soybean DNA. Amplification was in the presence of primer YRP (GGTGATGTCGGCGATATAGGCGCCAGCAAC) (SEQ ID NO:1), specific for the right arm of the YAC4 vector[13]. Lane 1 shows the amplification of purified vector (about 10 kb).

Figure 7:
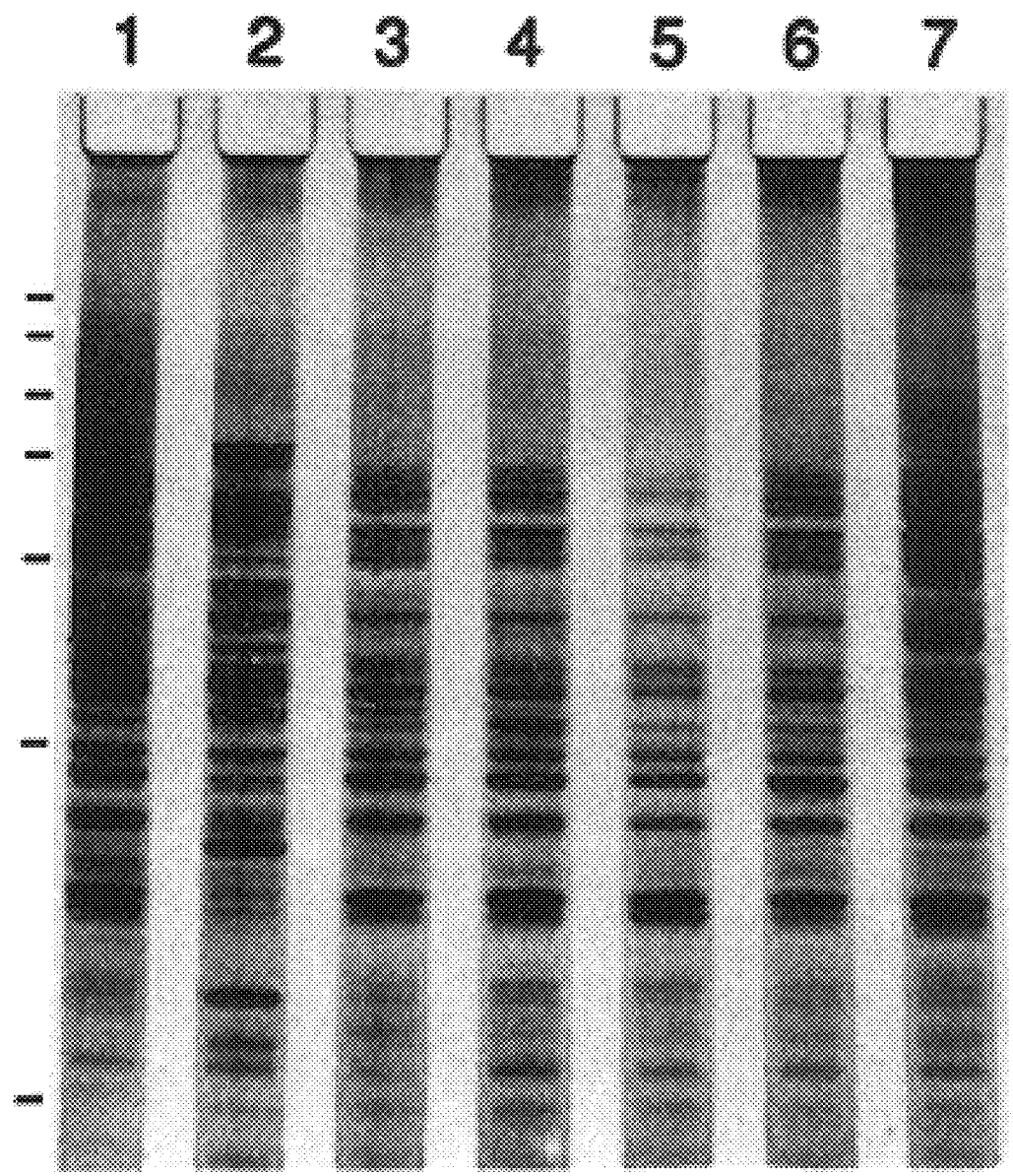
FIG. 7 shows profiles generated from a PCR product.

FIG. 7 shows DNA amplification of the PCR fragment pUTG-132a 1.1 kb STS defined by primers CACGGTCACTCATGGGCCATGG(SEQ ID NO:2) and CTGCAGAATTGGATTCCCAAAAGC(SEQ ID NO:3) in cowpea cv. California Blackeye (lane 1),. soybean cv. Bragg (lane 2), and soybean experimental lines AG102 (lane 3), AG107 (lane 4), AG112 (lane 5), AG114 (lane 6), and AG118 (lane 7).

Figure 8A:
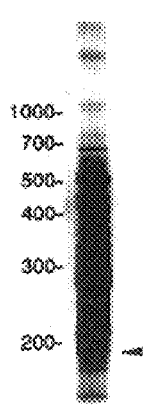
FIGS. 8A–C shows reamplification of a polymorphic isolated 180-bp DAF fragment from soybean DNA.
Figure 8B:
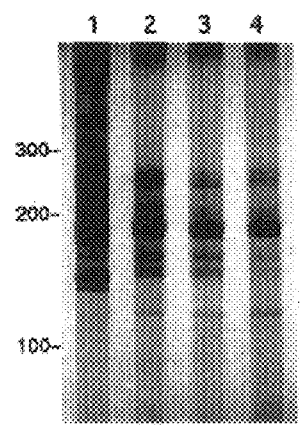
Figure 8C:
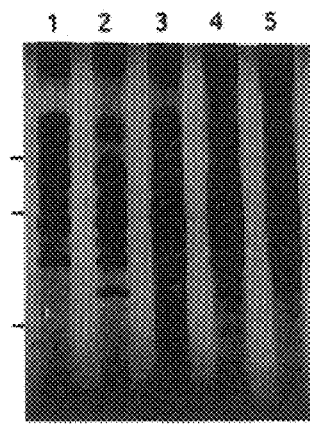

FIG. 8 shows the effect of polyacrylamide concentration on the isolation of a 180-bp DNA fragment from soybean. A polymorphic fragment (arrowhead) was isolated from a DAF profile (FIG. 9A) obtained from *Glycine max* L. Merr. cultivar Bragg using the arbitrary primer GATCGCAG and template predigestion with 3 restriction endonucleases. During isolation, amplification products were obtained following subsequent rounds of band excision, amplification and DNA separation in 6% (FIG. 9B) and 4.5% (FIG. 9C) polyacrylamide gels. The number of amplification rounds is indicated in each lane.

Figure 9:
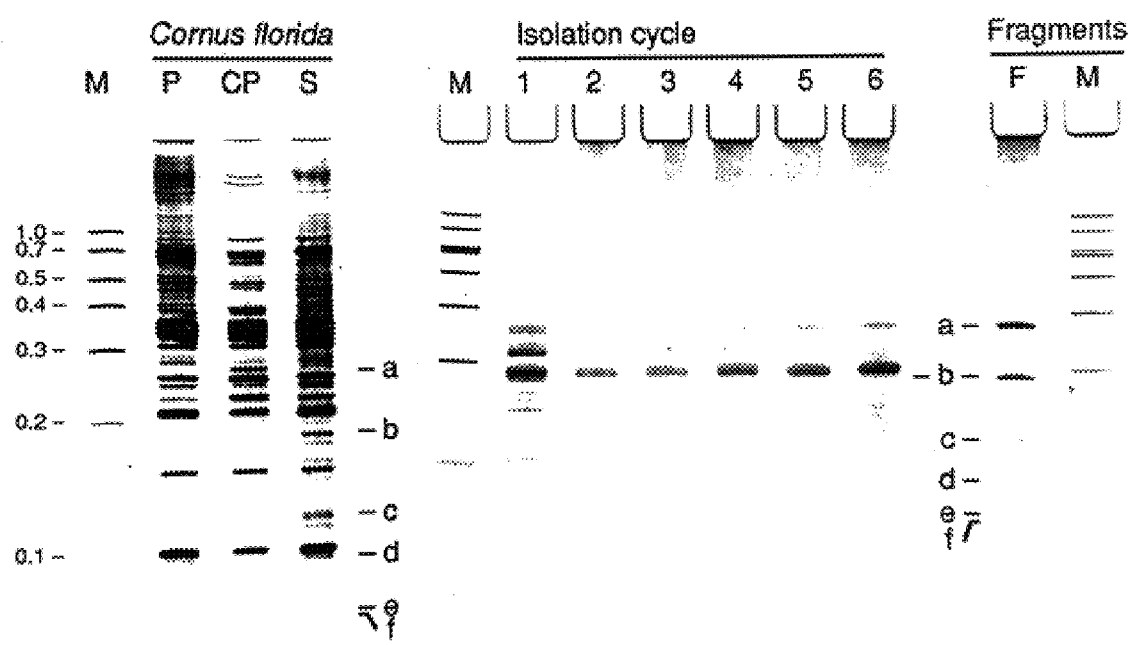
FIG. 9 shows reamplification of an isolated single DAF product in dogwood trees.

FIG. 9 shows isolation of DNA products from dogwood (*Cornus florida* L.) DAF profiles. Six polymorphic fragments that were part of DNA patterns generated from cultivars 'Cherokee Princess' (CP) (fragments a and f) and dogwood anthracnose-resistant 'Santamour' (S) (b and e) by amplification with the octamer primer GATCGCAG (left panel), were subjected to up to six cycles of isolation (band excision and subsequent amplification) as described in Methods. Aliquots of isolated fragments were pooled and electrophoresed together (lane F) (right panel). In most cases few isolation cycles were required. For example, only two isolation cycles of fragment b were necessary to eliminate most amplification contaminants (middle panel). Molecular weight markers (lanes M) are given in kb. Fragments present in 'Santamour' were also present in 'Presidential' (P), another tree putatively resistant to dogwood anthracnose.

Figure 10A:
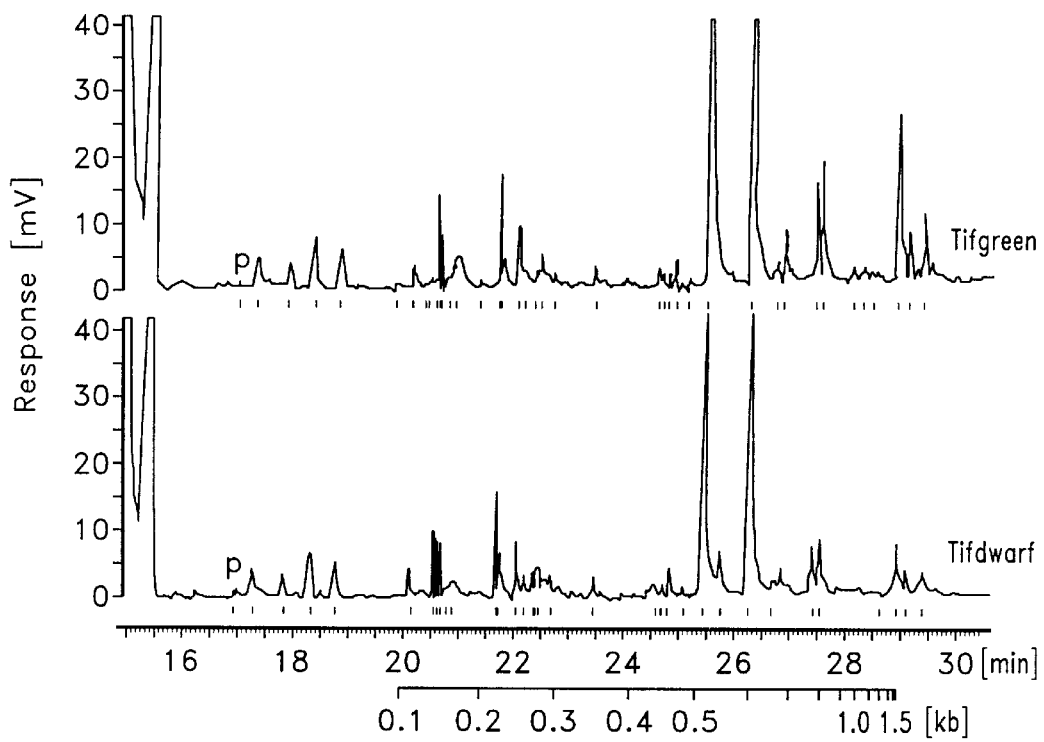
FIGS. 10A and B shows a comparison of DNA amplification profiles obtained by capillary electrophoresis (A) and by polyacrylamide gel electrophoresis (B).
Figure 10B:
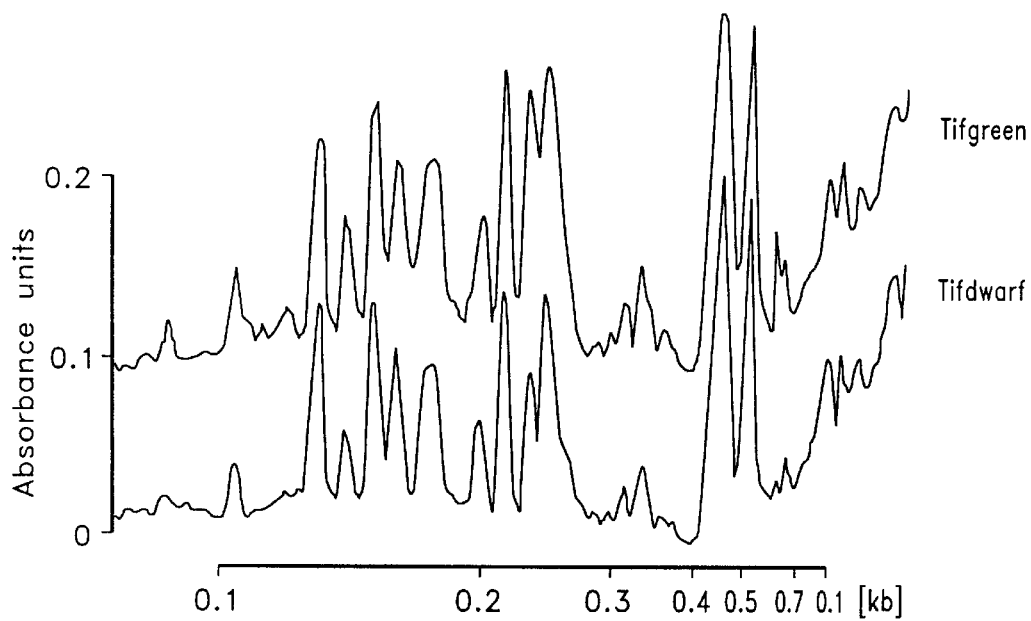

FIG. 10 shows the comparison of DNA amplification profiles resolved by capillary electrophoresis (FIG. 11A) and polyacrylamide gel electrophoresis (FIG. 11B). DNA from cultivars Tifgreen and the natural mutant Tifdwarf were amplified with primer GTTACGCC. A DNA polymorphic peak present in Tifdwarf is indicated by an arrowhead.

Figure 11:
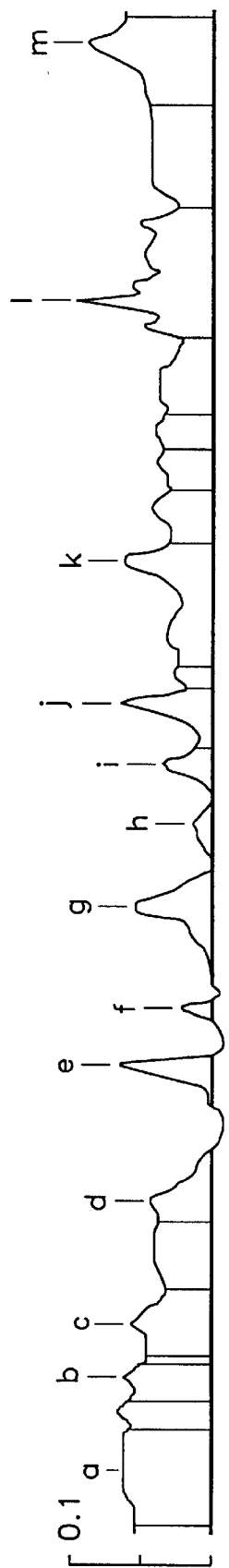
FIG. 11 shows a laser densitometric scan of a DNA fragment pattern generated from plasmid DNA.

FIG. 11 shows a laser densitometric scan of a DNA pattern generated from plasmid pUC18 with mini-hairpin primer $HP_7$-CTG. Each lettered peak of the scan corresponds to a visually determined band on a silver stained polyacrylamide gel containing the fragments produced following amplification with the primer. Molecular weights of the bands ranged from 103 to 971.

DESCRIPTION OF THE INVENTION

One embodiment of the invention is a novel oligonucleotide construct which is a primer complementary to simple sequence repeats ("SSR primer"). SSR primers, when used in accordance with the method of the invention, target microsatellite repeats in a nucleic acid, especially in DNA. A microsatellite repeat is a segment of the nucleic acid which contains a repeating sequence of two or more bases. The repeating bases may be any combination of A, T, C, and G.

The SSR primers are complementary to a microsatellite repeating sequence of a DNA template. For example, an SSR primer containing the two base repeating sequence $(GC)_6$ is complementary to the microsatellite repeating sequence $(CG)_6$. Likewise, an SSR primer containing the three base repeating sequence $(ATC)_5$ is complementary to the microsatellite repeating sequence $(TAG)_5$, and an SSR primer containing the five base repeating sequence $(GTTAG)_4$ is complementary to the microsatellite repeating sequence $(CAATC)_4$.

Typically, the SSR primer also contains a sequence of one or more degenerate bases. The degenerate base, represented by the symbol "N", may be any of A, T, G, and C, and therefore when present in the primer will define the primer as being composed of a number of molecular species. The number of these primer molecular species will be determined by the number of degenerate bases in the primer. Alternatively, the degenerate base may be a base able to pair with more than one of the bases present in the nucleic acid (such as A, G, C and T). Examples of such degenerate bases are hypoxanthine (I), 6H,8H,4-dihydropyrimido[4,5c][1,2] oxacin-7-one (P), and 2-amino-6-methoxyaminopurine (K). The sequence of degenerate bases may be from 1 to 10 bases in length, such as between 2 and 5 bases in length. In a preferred embodiment, the sequence of degenerate bases is 3 bases in length. The sequence of degenerate bases may be attached to either the 3' or 5' of the repeating sequence. The SSR primers may be referred to as $(B_x)_n(N)_m$ where the degenerate bases are attached to the 3' end of the repeating sequence or $(N)_m(B_x)_n$ where the degenerate bases are attached to the 5' end of the repeating sequence, where B is A, T, G, or C and where each subsequent B may be the same as or different than the preceding Bs, typically there being at least two different Bs in the repeating sequence, x is a whole number from 2 to 5, n is a whole number from 2 to 10, preferably, n=3 to 6, N is a degenerate base, and m is a whole number from 1 to 10, preferably m=2 to 5, such as 3.

The SSR primer described above, containing an SSR sequence and a degenerate base sequence, is referred to as a "simple" SSR primers. SSR primers can also be "complex", having the above two components plus an additional arbitrary sequence.

The arbitrary sequence has one or more bases, such as 1 to 25 bases, preferably 2 to 10 bases, and is attached to the SSR sequence and/or the degenerate base sequence, and may be positioned between or within the SSR and degenerate base sequences. Thus, the complex SSR primers may have the following formulas: $(R)_y(B_x)_n(N)_m$, $(R)_y(N)_m(B_x)_n$, $(B_x)_n(R)_y(N)_m$, $(B_x)_n(N)_m(R)_y$, $(N)_m(R)_y(B_x)_n$, or $(N)_m(B_x)_n(R)_y$, where B, x, n, N, and m are as described above, and R is a nucleotide G, C, A, or T, and y is a whole number from 1 to 25.

Because microsatellite regions of DNA are highly variable, targeting these regions by the use of SSR primers allows for the increased detection of polymorphic DNA and, importantly, for the detection of a high number of allelic forms of the targeted locus. Because primers complementary to the microsatellite (the SSR) will recognize all microsatellites in the genome, one needs to subselect only a fraction of the SSR loci by using sequences that immediately border the SSR. Preferably, arbitrary flanking sequences that target these bordering sequences are used if the number of originally targeted SSR is very high or degenerate flanking sequences if the number is low, as in a DAF profile.

SSR primers may be constructed by any of several methods known to those skilled in the art for synthesis of oligonucleotides. Examples of suitable methods of construction of synthetic oligonucleotides are found in Sambrook, et al., *Molecular Cloning*, Cold Spring Harbor, and in Ausubel, et al., *Current Protocols in Molecular Biology*, John Wiley & Sons, Inc., both of which are incorporated herein by reference.

As taught in the parent applications, the DAF process produces nucleic acid profiles of high specificity to produce a "fingerprint" characteristic of the nucleic acid template. The first DAF parent application taught the use of arbitrary primers at least 5 nt in length ("unstructured" primers) to produce DNA profiles with high multiplex ratios. Preferably, the unstructured primers are 5 to 25 nt in length.

The second DAF parent application taught the use of extraordinarily stable mini-hairpin primers harboring a "core" arbitrary sequence at the 3' terminus to amplify a wide range of templates ranging from plasmic DNA to plant and animal genomes. The core sequence may be constituted of any sequence of at least 3 bases. Typically, the core sequence is 3 to 8 bases in length, although the core sequence may be up to 25 bases in length. In addition to the core arbitrary sequence at the 3' end, the mini-hairpin primers contain a fixed sequence which forms a mini-hairpin. The mini-hairpin contains a stem of at least 2 annealed base pairs. Preferably, these base pairs are GC base pairs, although other base pairs, such as AT, may also be used. The mini-hairpins further contain a loop of at least 3 unannealed bases. Typically the loop contains 3 or 4 bases, but the loop may contain any number of bases so long as the mini-hairpin is stable. With loops having more than 4 bases, a stem of 3 or more base pairs may be used to maintain the stability of the mini-hairpin primer. The bases of the loop may be any of the bases G, C, T, and A, in any combination, and in any sequence. These mini-hairpin primers increase detection of polymorphic DNA or RNA and direct the controlled amplification of small template molecules, generating "sequence signatures" from plasmids, YACs, cloned DNA, and PCR amplified fragments. The mini-hairpin primers also increase detection of polymorphic DNA or RNA in complex templates, such as in bacteria, animals and plants. Additionally, the mini-hairpins may be modified, such as by adding a fluorophore label or biotin to the 5' end of the mini-hairpin, or by substituting degenerate bases in the primer sequence. These modifications result in alterations to profiles produced and may increase detection of polymorphisms.

It has been unexpectedly found that reamplification of the nucleic acid DAF products, using unstructured, mini-hairpin primers, or SSR primers to generate arbitrary signatures from amplification profiles (ASAP), increases significantly the detection of polymorphic nucleic acids. Whereas unstructured and mini-hairpin primers target no particular region of a genome, SSR primers target only those DAF products that have microsatellite repeat sequences. Because the SSR primer turns the microsatellite repeat sequence of a nucleic acid into a target, reamplification with an SSR primer allows for detection of polymorphism based on the highly variable microsatellites.

Reamplification to yield ASAPs which are highly variable increases detection of polymorphism. The ASAP approach allows for increased separation of closely related varieties of a species, such as closely related bermudagrass cultivars as shown in FIG. 1C and in detecting several linked markers in bulked segregant analysis of species such as soybean, as shown in FIGS. 1A and B.

The ASAP process of reamplification involves the initial annealing and amplification of a nucleic acid template using one or more primers and a nucleic acid polymerase, as taught in the parent applications. Prior to separation of the nucleic acid fragments so produced, the fragments are allowed to anneal to one or more primers different from that used for the initial amplification and are again amplified. Reamplification can be performed multiple times in order to maximize the detection of polymorphisms.

In essence, the reamplification procedure can be conceived of as a DAF upon DAF procedure or as a fingerprint of a fingerprint. However, in contrast to the one step DAF procedure, reamplification DAF is a multistep process.

Any combination of primers may be used for the initial and subsequent amplifications. The reamplification primer may be shorter, longer, or the same length as the primer for the initial amplification. For instance, an unstructured oligonucleotide may be used as the primer for the initial amplification, followed by a second amplification using a different unstructured primer or a mini-hairpin primer. Alternatively, a mini-hairpin oligonucleotide may be used to prime the initial amplification, followed by a subsequent amplification with an unstructured or a different mini-hairpin primer. Likewise, an SSR oligonucleotide primer may be used as the initial and/or the reamplification primer.

Primer concentration preferably is about 9 $\mu$M for unstructured primers and 6–9 $\mu$M for mini-hairpin primers.

Preferred range of template concentration for reamplification is between 0.001–1 ng/μl. Lower or higher concentrations of primer and/or template may be used as long as the fingerprint generated is reproducible. Similar profiles were obtained when patterns generated from soybean or bermudagrass DNA with the mini-hairpin primers $HP_7$-CTG or $HP_7$-AGA were amplified with mini-hairpin decamers with all possible single-base pair substitutions in the arbitrary core.

It is also within the scope of the present invention to use a nonarbitrary primer, such as a PCR primer, as either the initial or reamplification primer.

The reamplification technique can be used in conjunction with any nucleic acid template, from any source, whether the sequence of the template is known or unknown. Both RNA and DNA templates can be reamplified in this way. Reamplification of nucleic acid templates from various sources is illustrated in the Figures and in the Examples that follow.

Reamplification to generate ASAPs has been found to be particularly useful in localization of genetic markers by bulked segregant analysis ("BSA").

In BSA, a segregating population, which may be an animal, plant, fungal, bacterial, or viral population, is grouped into two or more pools, or bulks, according to the presence or absence of a selected phenotype. The genotype of each member of each bulk will differ but, because the members of each bulk share a common characteristic, that is presence or absence of the trait of interest, each member of each bulk will have polymorphic markers associated (or linked) with the characteristic or trait in study. Bulks can also be constructed according to the presence or absence of one or more markers, thereby basing the BSA on the genotypes of the sample. Typically, the locus codes for a phenotype which, when not present in mutant allelic form, results in a wild type phenotype.

The DNA of each bulk is pooled and each pool is subjected to DAF analysis. The identification of a DAF fragment in one pool which is not present in the other pool allows for identification of a genetic marker for the gene or trait of interest. Because genetic differences between bulks are typically minimal, reamplification of the fragments produced by DAF bulked segregant analysis may be performed to maximize the ability to detect a genetic polymorphism between the bulks. See FIGS. 2 and 3.

BSA can be used to genetically map a specific trait in the genome. Once a genetic marker is identified by BSA, the marker can be isolated and sequenced to produce a sequence characterized amplified region ("SCAR"). The derived SCAR can be used in physical mapping to order regional YAC or phage P1 clones or to initiate a directed walk to the gene. FIG. 4 depicts diagrammatically the use of BSA and SCARs to genetically map a specific phenotype.

Reamplification of an isolated amplification product, such as those obtained by DAF or PCR, which product may, for example, be removed from a polyacrylamide or agarose gel, collected by real time separation of amplification products such as by CE, or removed from a bound oligonucleotide in an oligonucleotide array, is useful to distinguish between closely related templates. Amplification products separated by length or by sequence polymorphism may be isolated and reamplified. DNA products from DAF profiles generated by amplification using unstructured oligonucleotide primers or mini-hairpin primers have been isolated directly from polyacrylamide gels. Products from profiles generated by other primers, such as PCR primers or SSR primers may also be isolated. The desired band representing monomorphic or polymorphic product of interest may be used directly as a source of template for further amplification. A gel segment containing the fragment of interest may be excised from a fresh or preserved gel with a flamed dissection probe or scalpel and placed in a standard amplification mixture. Any suitable method of removal of the gel segment may be used, so long as the fragment of interest is not disrupted during removal.

Subsequent rounds of amplification, DNA separation, and band isolation may be performed to produce a single strong band on the gel. The isolation of products of up to 500 bp in size usually involves 3 to 5 rounds of isolation by amplification. If an amplification appears to fail, that is, does not produce a band or does not produce separation of bands, subsequent amplification using the "failed" reaction mixture as template will generally produce the desired products.

FIG. 5 shows the isolation of a 200-bp product from a DAF fingerprint obtained from "Tennessee Hardy" centipedegrass. The product was isolated after 3 rounds of amplification, band excision and separation in 5% polyacrylamide gels, and used as a probe for Southern hybridization to centipedegrass DAF patterns transferred to nylon membranes. Only a single product was observed in autoradiograms. Hybridization to several centipedegrass cultivars confirmed its monomorphic nature.

Polyacrylamide gel concentration influences DNA fragment isolation. For example, isolation of a 180-bp marker, one of several found tightly linked to a developmental locus controlling nodulation in soybean, required 5 rounds of amplification in 4.5% polyacrylamide gels. In contrast, only 3 isolation rounds were needed when 6% gels were used. Loading the gels with lower amounts of template did not alter the efficiency of band isolation.

The direct isolation of DAF products from silver-stained gels can easily generate probes for Southern hybridization. These probes can be used to determine if the amplification product represents a single or multi-locus site in the genome or to confirm its absence from other DAF patterns. With this purpose, we have isolated many DAF products generated from bacteria, fungi, and plants, such as centipedegrass and soybean. Isolated DAF products that have and have not been subsequently cloned gave virtually the same genomic hybridization results. Therefore, DNA fragments isolated by amplification can be used directly as probes without further subcloning or can be subcloned for DNA sequencing without further purification.

DAF products have been isolated directly from silver-stained gels bound to polyester backing films that have been stored dried for more than 2 years. DNA isolation from preserved fingerprints may be especially important when genetic evidence is entered in a court of law, for plant variety rights enforcement and related deposition requirements or for retrospective examination and extended study of interesting genetic material.

The separation of amplification nucleic acid fragment products by polyacrylamide or agarose gel electrophoresis, usually followed by silver staining, is taught in the parent applications. The separation is followed by the determination of the characteristic pattern of fragments by visualizing the characteristic pattern of the nucleic acid on the dried and developed gel. Separation of DAF products can be obtained by other methods, however, which can be used in place of or together with gel electrophoresis. These other separation methods may or may not result in increased detection of nucleic acid polymorphism.

One such suitable method of separation is by capillary electrophoresis (CE), which may be performed, for example, by dynamic sieving electrophoresis (DVE), or by capillary gel electrophoresis (CGE). In one embodiment, CE allows for the sequential separation of nucleic acid fragments in real time. In CE, the electrophoresis of nucleic acid fragments is performed through a matrix, which may be a gel matrix, which is in a capillary tube, as opposed to standard methods of electrophoresis wherein the gel is on a slab. As in standard slab gel electrophoresis, with CE, the fragments migrate through the matrix at different rates, based primarily on the size of the fragment. CE, however, permits the fragments to be detected individually, as the fragments may be collected in real time, as they migrate out of the capillary tube at different times.

One interesting aspect of capillary electrophoresis is that the separation, collection, and determination of fragments may be automated. Several methods and apparatuses for automated capillary electrophoresis are known which may be used in conjunction with the DAF technology.

A second method is Denaturing Gradient Gel Electrophoresis (DGGE), whereby the polyacrylamide or agarose gel has a pH or a temperature gradient over the course of migration of double stranded DNA fragments. Alkaline pH or elevated temperatures cause the DNA to denature, which causes slowing of the migration and increased separation of bands.

A third method is separation of DAF fragment products, not by length polymorphism, but by sequence polymorphism. One suitable process for separation of DAF products by sequence polymorphism is by the use of oligonucleotide arrays bound to solid supports.

An amplified DAF sample is labelled and hybridized with a two-dimensional array of surface-bound oligonucleotides. Alternatively, the array can be composed of particles containing bound oligonucleotides. These particles may be beads. The beads can be in solution and after hybridization can be deposited by sedimentation, centrifugation or by a magnetic field if the beads are para-magnetic. These particles or beads can be labelled with specific tags characteristic of each bound oligonucleotide or can vary in size or property, the sizes or properties being characteristic tags of each bound oligonucleotide. Ulterior discrimination of these particles or beads then renders a specific assay.

As an example, the particles can be beads of different sizes, each size class corresponding to one oligonucleotide sequence. Following hybridization of the amplification products, which have been previously labelled, to the beads, the beads are separated by size and analyzed for positive hybridization signals.

The number of oligonucleotides in an array may vary from few to a few hundred or thousands, depending on the ability to set them in a two-dimensional solid support. Nucleic acid polymorphisms that alter the amplification with arbitrary primers or alter the ability to hybridize to the oligonucleotide probes of the array are expected to produce specific changes in the resulting "hybridization fingerprint". These changes are seen as variations in those oligonucleotide probes able to hybridize successfully with the amplification products.

The invention therefore proposes a two-step sampling of a DNA template, the first through amplification with arbitrary oligonucleotide primers, the second through hybridization of amplified products with an array of short oligonucleotide primers. During the first step, a complex genome such as soybean or human (containing about $10^6$ kb) may render, depending on the primer used, 10–100 kb of sequence. During the second step, this small sample of the original genome analyzed is screened and subselected by hybridization to the array. The number of positive hybridizations in the array will depend on the length of the hybridization probes and on the number of oligonucleotides in the array. For example, an array of 9-mer or 10-mer oligonucleotides will contain about 40% to 10% of positive hybridizations, respectively. An increase in the length of the oligonucleotides used will therefore decrease the number of positive hybridizations in the array. Fine tuning between the length of the probes, the size of the array, the complexity (length) of the nucleic acid in study (being it DNA or RNA), and the primer used to amplify the original template, will be required.

The arrays may consist of a collection of small oligonucleotides of differing sequence. The oligonucleotides may be from 3 to 5 nucleotides in length although shorter or longer oligonucleotides may be used, for example 4 to 12 nucleotides, or 6 to 10 nucleotides, preferably 8 to 10 nucleotides in length. The unseparated DAF fragment products are permitted to anneal to the bound oligonucleotides in the array. Thus, because the DAF products will anneal to oligonucleotides based on the complementary sequences of the DAF products and the bound oligonucleotides, the fragments are separated and analyzed, not by length polymorphism, but by sequence polymorphism. The pattern of differential hybridization of the fragments produces a characteristic profile, or fingerprint, of the template.

In a preferred embodiment, the DAF reaction is performed with labelled oligonucleotides, such as $^{32}P$ or fluorophore labelled deoxyribonucleotides. The pattern of hybridization of the radioactive DAF products to the membrane bound oligonucleotides is determined by an analysis of the pattern of emitted radiation. The analysis can be accomplished by exposure of the array to photographic film, or by direct measurement of emitted radiation. Alternatively, the recorded or digitized hybridization pattern could be entered into a computer, and using a suitable program, it could be analyzed and made visible on the monitor screen or on a hard-copy computer printout. The program could compare one or more of these "digitized fingerprints" and could reveal similarities or differences between the nucleic acid hybridization profiles. The use of oligonucleotide arrays is described in Chetverin, "Oligonucleotide Arrays", Biotechnology, 12:1093–1099 (1994), which is incorporated herein by reference.

The DAF methodology, including that taught in the parent applications and the advances taught in the present application, including reamplification, is preferably performed as follows.

Using any primer, DAF is preferably performed in the presence of magnesium ion, preferably in the form of $MgSO_4$, although good profiles are obtained with $MgCl_2$. Replacing $Mg^{+2}$ with other cations, such as $Ca^{+2}$, $Ba^{+2}$, and $Sr^{+2}$, generally results in inferior profiles. Levels of magnesium can be 1.5 to 12 mM. Generally, for optimum profiling of complex nucleic acid templates, such as animal or plant templates, lower concentrations of magnesium are preferred, between 1.5 to 4 mM or 6 mM. For profiling simple templates, such as bacterial, fungal, mitochondrial or chloroplast DNA, or amplification products such as those obtained by PCR, magnesium concentrations as high as 8 mM, such as between 3 or 4 to 8 mM may be used with good results. Generally, magnesium concentrations between 3 and 6 mM produce optimal results with most templates.

The concentration of primer is preferably at least 1.5 $\mu M$. Generally, higher primer concentrations (up to 30 $\mu M$)

increases the efficiency of amplification without altering DNA profile composition. Reproducible patterns of PCR fragments, plasmids or lambda phage are preferably obtained with higher primer concentrations (about 30 $\mu$M). Generally, a minimum of 5 ng/$\mu$l, 1 ng/$\mu$l or 0.1 ng/$\mu$l of template DNA from plasmids, low, or high complexity genomes, respectively, is preferred.

Three preferred optimized buffer formulations were found which, in combination with MgSO$_4$, produce good quality DAF profiles. TTNK10 (20 mM Tris-HCl, 0.1% Triton X-100, 4 mM (NH$_4$)$_2$SO$_4$, and 10 mM KCl) TTK10, and TTK30 (20 mM Tris-HCl, 0.1% Triton X-100, and 10 mM or 30 mM KCl, respectively). These formulated optimized buffers can support wide pH and MgSO$_4$ ranges. Other buffer formulations which are suitable for use with the method of the invention can be determined by one skilled in the art.

Preferably, the GC content of unstructured or mini-hairpin primers is at least 50%, although any GC content can be used. No increase in complexity of obtained profiles is observed with primer percentages of GC higher than 50%.

The DAF technology has widespread applicability to templates from any source. Nucleic acid templates from monocotyledonous and dicotyledonous plants, including grasses such as turfgrass and crops such as soybean, vertebrate and non-vertebrate animals, yeast, fungi, bacteria, and viruses have been successfully profiled with DAF. Subgenomic and nongenomic nucleic acid templates are also successfully profiled with DAF.

Short mini-hairpin primers are especially suited for the analysis of low complexity genomes and small DNA molecules. One particularly interesting such application is the use of DAF with artificial chromosomes, such as YACs, BACs or MACs. For example, like plasmids, YACs have selectable markers and a cloning site and allow for the insertion of DNA. The YAC carrying the foreign DNA can be transfected into a yeast cell. Once in a yeast cell, YACs are heritable. Unlike plasmids which can only be transformed with up to about 25 kilobases, YACs can be transformed with sequences which are megabases in length.

Because YACs can be transformed with such large DNA sequences, the use of YACs allows for very large steps in gene walking. However, YACs often have repeated and chimerical DNA sequences, complicating their use in gene walking. To alleviate this problem, DAF may be used to determine and locate non-repeating DAF products from YACs. Alternatively, bacterial artificial chromosomes (BAC) or mammalian artificial chromosomes (MAC) can be used to clone high molecular weight DNA. The use of BACs and MACs, which can also be analyzed using DAF, may decrease problems of chimeras within insert DNA.

FIG. 6 shows various fingerprints obtained when amplifying YACs containing 100–333 kb of cloned soybean DNA with a mini-hairpin and a YAC4 vector-specific primer. Many of the amplified products contain terminal sequences from the cloned soybean DNA that can be used as sequence tagged sites (STSs) for genetic and physical mapping. The YAC-characteristic fingerprints were produced despite the presence of common yeast genomic DNA background, making DAF analysis a superior alternative to Alu-PCR analysis of YAC DNA. The example in FIG. 6 shows how DAF profiling can be accomplished using a PCR primer specific to one of the ends of a YAC vector together with a mini-hairpin primer that screens arbitrary sites in the soybean template. The profiles shown in FIG. 6 illustrate the general applicability of DAF with both specific and arbitrary primers.

Another promising use of DAF with YACs is in the analysis of cloned DNA with mini-hairpin primers to confirm identification of overlaps in YACs and cosmid libraries for genome analysis.

The DAF technology, especially with mini-hairpin primers, can be used in generating profiles of subgenomic DNA, such as mitochondrial DNA, chloroplast DNA, or of small DNA molecule templates, such as plasmids, cloned DNA material in phage or plasmid DNA, or PCR amplification products.

In the latter case, DAF may be used much like restriction endonuclease analysis. Consistent DAF profiles were generated from a 1.1 kb PCR product defining a STS within pUTG-132a, a marker tightly linked to the nts locus in soybean.

DAF has been used successfully in systems having more than one template. This technique has particular value in situations where the separation of the templates is desired, such as in distinguishing pathogenic DNA from host DNA.

With DAF, where the template is composed of more than one genome, it is possible to differentiate each organism without resorting to physical separation of the contributing genomes. In the study of the Azolla-Anabaena symbiosis, selective characteristic DAF profiles for the fern or the cyanobacterial symbiont have been generated by altering primer sequence.

In this manner, DAF may be used to fingerprint isogenic infected and uninfected tissue and distinguish amplification products that stem from the pathogen. The diagnostic DAF product can be cloned directly from a silver stained gel, and used as a hybridization probe. Alternatively, partial sequencing may direct the synthesis of two specific PCR primers that amplify a diagnostic PCR product detectable by electrophoresis or presence of incorporated fluorophores.

DAF can be used with one or more primers in each amplification reaction, these primers being one or a combination of specific, hemispecific, hemiarbitrary, arbitrary, hemidegenerate, or degenerate primers. Profiles generated with a combination of primers are different than those generated using a single primer. By combining primers, it is possible to increase the number of different profiles produced from a limited number of primers. Furthermore, the combination of a specific and an arbitrary primer can allow the generation of products around a defined region in a template. For an example, see FIG. 6.

Because DAF products are heritable, the DAF technology is particularly well suited for use in the diagnosis of heritable diseases, both in plants and in animals, such as for cystic fibrosis. DAF may also be useful in isolating the causative gene.

The following examples are provided for illustrative purposes only and the invention is not to be so limited. Whereas a particular aspect of the DAF technology may be exemplified with a particular primer or a particular template, it is contemplated that any primers, of any type or sequence, may be substituted for the exemplified primer, and a nucleic acid template from any source and of any size may be substituted for the exemplified nucleic acid.

EXAMPLE 1

DAF Reactions

DAF reactions were in a total volume of 10–25 $\mu$l (usually 20 $\mu$l) and contained 3 $\mu$M primer, 0.3 units/$\mu$l AmpliTaq Stoffel fragment DNA polymerase (Perkin Elmer-Cetus, Norwalk, Conn.), 200 μM of each deoxynucleoside triphosphates (USB, Cleveland, Ohio), 0.1 to 5 ng/μl of template DNA (isolated using established protocols; cf. 4), and 1.5 mM MgCl$_2$ and Stoffel buffer (10 mM KCl, 10 mM Tris-HCl; pH 8.3) when using unstructured primers, or 4 mM MgSO$_4$ and TTNK10 buffer (10 mM KCl, 4 mM (NH$_4$)$_2$SO$_4$, 0.1% Triton X-100, 20 mM Tris-HCl; pH 8.3), when using mini-hairpin primers. The mixture was amplified in a recirculating hot-air thermocycler (Bios, New Haven, CT) for 35 cycles of 30 s at 96° C., 30 s at 30° C., and 30 s at 72° C.

Amplification products were separated in polyester-backed 5% polyacrylamide-7M urea slab mini-gels. Wells were loaded with about 3 μl of a 1:5 dilution of each amplification mixed with 3 μl of loading buffer (10 M urea, 0.08% xylene cyanol FF), and electrophoresis run at 120 V for approximately 75 min. DNA was detected at the picogram level by silver staining, as taught in U.S. patent application, Ser. No. 07/676,869, incorporated herein by reference. Backed gels were preserved by drying at room temperature. Denaturing 20% polyacrylamide-7M urea gels and silver staining were used to resolve DNA oligomers, determine their electrophoretic mobilities, and detect alternative molecular species.

EXAMPLE 2

Reamplification to Produce an Arbitrary Signature for Amplification Profile (ASAP)

Reamplification with a primer, either an unstructured primer or a mini-hairpin primer, was performed using the same technique and components as the initial DAF reactions as in Example 1, except that primer concentrations were about 9 μM, and template concentrations were about 0.1 ng/μl. The primer concentration for reamplification using primers complementary to single sequence repeats (SSR primers) was about 3 μM.

FIG. 1A shows initial DAF amplification of several bulked pools of soybean DNA using an unstructured 8-mer primer. FIG. 1B shows subsequent reamplification using mini-hairpin primers HP$_7$-GAT and HP$_7$-CGA and using SSR primers NN(AG)$_6$. FIG. 1C shows reamplification with NN(AG)$_6$ of four closely related bermudagrass cultivars which were initially amplified with the unstructured primer CCTGTGAG. Reamplification of these same four bermudagrass cultivars was also performed successfully with SSR primers NN(CT)$_6$ and NN(TG)$_6$. Reamplification is also performed successfully with SSR primers (AG)$_6$NN, (CT)$_6$NN, and (TG)$_6$NN.

Despite the highly conserved nature of the nts region, ASAP with just a few mini-hairpin primers identified several polymorphisms between the bulks. The arbitrary selection of primers was also biased to include recognition of particular sequence motifs within the genome or the DAF profile that would either increase or decrease polymorphic content or target specific genomic regions. For example, primers were derived from sequence arrays in repetitive DNA, such as SSRs present in microsatellites. The advantage of targeting these highly polymorphic regions is that generated markers are usually co-dominant and express many allelic variants. ASAPs were produced by reamplification of DAF fingerprints with degenerate 5' anchored SSR primers. ASAPs are also produced by reamplification with degenerate 3' anchored SSR primers.

ASAP with SSR primers was also effective in differentiating closely related bermudagrass cultivars. See FIG. 1C.

Upon initial DAF profiling, Cultivars Tifway II (γ-irradiation induced mutant of Tifway) and Tifdwarf (natural somatic mutant from Tifgreen) proved very difficult to differentiate from their close parents. ASAP analysis with only 3 primers identified several polymorphisms, and enabled the identification of a group of 13 established bermudagrass cultivars.

EXAMPLE 3

Isolation and Reamplification of a Single Amplification Product

An initial DAF fingerprint was produced from DNA from centipedegrass using the unstructured primer AACGGGTG. The DAF reaction products were separated in polyacrylamide gel and were silver stained. A 200 bp product was excised by a scalpel from the gel and used as a template for reamplification, using the same primer. Only a single DAF ASAP product was obtained after 3 rounds of amplification, confirming the monomorphic nature of the isolated 200 bp product. See FIG. 5.

Reamplification of a polymorphic isolated 180 bp DAF fragment from soybean DNA produced by initial DAF reaction with an unstructured primer GATCGCAG allowed for an increased detection of polymorphism when reamplified. Five rounds of reamplification were used to provide adequate separation using 4.5% polyacrylamide, whereas only 3 reamplification rounds were necessary on 6% polyacrylamide. See FIG. 8.

Reamplification of isolated DAF products was also performed using one or more primers which differ from the primer of the original amplification in sequence, length, and/or type of primer. Reamplification using an unstructured primer, a mini-hairpin primer, or an SSR primer is performed on DAF products obtained following amplification with an unstructured primer, a mini-hairpin primer, or an SSR primer. The ability to detect nucleic acid polymorphisms is increased following such reamplification.

EXAMPLE 3A

Reamplification of Isolated Amplification Products

FIG. 9 shows band isolation from relatively complex DAF profiles generated from two cultivars of flowering dogwood (Cornus Florida L.), an ornamental tree native to the eastern deciduous forests of North America. The dogwood has been threatened by the introduced fungal pathogen *Discula destructive* Red., which causes anthracnose and devastation in native tree populations. Here DAF was used to find markers diagnostic of disease-resistant trees.

Bands that were common between cultivars shown putatively resistant to the disease but polymorphic with those that were susceptible were selected. Candidate bands generated from the anthracnose-resistant cultivars "Santamour" and the susceptible "Cherokee Princess" were recovered free of major contaminants in only 2–3 isolation cycles.

EXAMPLE 4

Separation of DAF Products by Hybridization

Amplification products generated by DAF can be analyzed by hybridization to oligonucleotide arrays. The array is composed of a group of oligonucleotide probes arranged in a two-dimensional manner on a surface support, or in liquid bound to solid supports that are appropriately tagged. The amplification products are labelled and allowed to hybridize specifically with the array. The label provides a way to identify which probes rendered positive hybridization.

It may be necessary in some instances to decrease the size of the amplification products before hybridization to the array. This can be accomplished by random rupture of the nucleic acids by physical means, such as by sonication or ultraviolet light.

Oligonucleotide arrays can be prepared in a number of ways. For example, oligonucleotides can be synthesized by methods such as that of Beattie (Beattie et al., 1988; Beattie and Fowler 1991), listed in the Bibliography below and incorporated herein by reference. Oligonucleotide probes are attached to a glass surface, the glass slides having previously been treated with nitric acid and rinsed with water, hexane, acetone and ethanol. The glass slides are soaked for several hours at 85° C. in 24:8:1 of xylene/γglycidoxypropyltrimethoxysilane (epoxysilane) / N,N-diisopropylethylamine. Attachment of 5' or 3'-aminoalkyl-derivatized oligonucleotides to the activated glass surface through reaction between terminal amine and epoxy groups is achieved by spotting the derivatized oligonucleotides to the glass surface, overnight incubation at 60° C., washing with water, 10 mM triethylamine (pH 9), and water. Plates are then stored dry for further use. Other alternative protocols are available. For example see Southern et al. (1994), listed in the Bibliography below and incorporated herein by reference. Hybridization can be carried out using conditions described by Dramanac et al. (1990), listed in the Bibliography below and incorporated herein by reference. Slides are preincubated overnight with Blotto at 37° C., rinsed with hybridization solution (3.3 M tetramethylammonium chloride, 60 mM Tris-HCl (pH 8), 0.1% SDS, 2 mM EDTA, 10% polyethylene glycol). The labelled ($^{32}$P) amplification products are dissolved in the hybridization solution, and 10–20 μl of this solution is applied to the array and incubated at 6° C. for at least 2 h. The array is washed with hybridization solution, dried and exposed to an x-ray film.

Oligonucleotide probes can also be covalently bound to thin $SiO_2$ films on surface matrices (Lamture et al., 1994), listed in the Bibliography below and incorporated herein by reference. Radioactively labelled amplification products are then hybridized to the probe matrix under conditions of high stringency, and the matrix is placed directly on the surface of a charge coupled device (CCD) which is used to detect radioactive decay from hybridized amplification molecules. Alternatively the oligonucleotide probes can be attached directly to the surface of the CCD.

Hybridization probes can be layed in nylon filters as described by Maier et al (1994), listed in the Bibliography below and incorporated herein by reference. Fluorescent labelled probes using fluorescent substrates such as Attophos (Maier et al. 1994) or labelled at the 3' or 5' with biotin or digoxigenin (DIG) are hybridized at 50–200 nM probe concentration overnight in 4×SSC, 7.2% sarcosyl at 8° C. Filters are washed at 8° C. for 15–30 min in the same buffer followed by 30 min incubation in streptavidin-alkaline phosphate conjugate in 4×SSC/5% sarcosyl at 8° C. (for biotin labelled oligonucleotides), unbound conjugate removed by one wash in the same buffer, 2 washes in 2×SSC and one wash in washing buffer (100 mM Tris-HCl (pH9) (8° C.), 600 nM NaCl, 1 mM $MgCl_2$). A solution of 1 mM Attophos in 2.4 M diethanolamine pH10, 1 mM MgCl2, and 0.01% sodium azide is diluted in washing buffer to a final concentration of 0.3 mM and sprayed on the membrane. The membrane is wrapped and exposed to X-ray film. DIG-11-dUTP labelled oligos can also be used (Maier et al 1994).

Alternatively, oligonucleotide probes can be immobilized onto 96-well ELISA plates as described in Nikiforov et al (1994), listed in the Bibliography below and incorporated herein by reference. Double stranded amplification products are rendered single stranded with the enzyme T7 gene 6 exonuclease, and captured onto individual wells of a 96 well polystyrene plate by hybridization to an immobilized oligonucleotide primer.

EXAMPLE 5

Real-Time Separation of DAF Products by Capillary Electrophoresis (CE)

CE separation of DNA fragments was performed using an ABI 270A-HT CE system (Applied Biosystems, Foster City, Calif.) fitted with a fused-silica capillary tube (75 μm ID, 70 cm, 50 cm effective length) and using ABI DNA Fragment Analysis Sieving separation chemistry, modified by addition of 20% urea and 10 μM ethidium bromide. Prior to analysis, the capillary tube was flushed with 0.3 N NaOH, distilled deionized (DI) water, 5N HCl, and DI water for 1 min each, and then rinsed with sieving polymer for 8 min. Electrophoresis was run at 210 V/cm and 30° C., using reverse polarity, and products detected at a wavelength of 260 nm. All sample injections were performed electrokinetically at –7 KV for 5 sec. Samples were prepared for analysis by membrane dialysis. Amplification reactions were placed as a single drop on top of a VS 0.025 μm membrane (Millipore Inc., Bedford, Mass.) floating on water, and allowed to dialyze for 20 min. Size calibration used a 100 bp ladder (Gibco BRL, Gaithersburg, Md.).

Highly reproducible DNA profiles were generated when DAF products were resolved using the ABI DNA Fragment Analysis Sieving separation chemistry in the presence of urea and ethidium bromide. Generation of DNA profiles required dialysis of samples prior to electrokinetic loading. CE separated DAF products with high resolution and reproducibility within the size range of molecular mass standards (100–1500 bp) used for calibration. Furthermore, electrophoretograms showed reproducible peaks of high molecular weight, indicating that while our DAF protocol allowed reproducible amplification of products over 1500 bp in size, CE resolved these products efficiently. CE electrophoretograms and scanned DAF silver stained profiles produced from bermudagrass cultivars Tifgreen and Tifdwarf were compared. See FIGS. 10A and B. CE allowed for the detection of polymorphic bands which were not detectable by slab electrophoresis. For example, a group of four monomorphic bands with retention times ranging 17–19 min, see FIG. 10A, were reproducibly detected in all 11 bermudagrass cultivars examined. However, polyacrylamide gel electrophoresis and silver staining was unable to detect them. Furthermore, silver stained profiles could not clearly distinguish the two bermudagrass cultivars. In contrast, CE detected the existence of a single polymorphic fragment present in Tifdwarf, the somatic mutant.

The high resolution and reproducibility of CE gives the technique the potential for its use in routine DNA analysis. Separation is complete in about 30 min, while automatic loading increases throughput with unattended operation.

EXAMPLE 5A

Capillary Electrophoresis by Dynamic Sieving Electrophoresis

Dynamic sieving electrophoresis (DSE) is performed using a phosphate buffer system consisting of 0.1M sodium phosphate, pH 8.0. The buffer is prepared with HPLC grade water. The sieving agent, hydroxyethylcellulose (HEC) is prepared as a 2% solution and then added to the buffer. The solution is stirred for several hours until the polymer is fully dissolved. The buffer system is filtered (0.45 μm) before use to remove any particulates. Ethidium bromide (EB) is added to the buffers immediately before use at final concentration of 10 μm.

DSE is performed on ABI 270A-HT capillary electrophoresis system (Applied Biosystems, Foster City, Calif.) using reverse polarity (positive potential at the destination end of the capillary). The temperature is set at 30° C. and UV absorbance is set at 260 nm. Data collection and analysis is performed using the Dionex A1450 Data System (Dionex, Inc., Sunnyvale, Calif.).

Primer mediated amplification of nucleic acids is performed as in Examples 1 and/or 2 above. Separations are performed using 100 μm i.d. DB-17™ surface modified fused silica capillary (50 cm length, 30 cm effective length), 50% phenylmethyl silicon stationary phase (J&W Scientific, Folsom, Calif.) with the phosphate buffer. Capillaries are flushed with sieving buffer for 5 minutes prior to the first run. Samples are injected into the capillary by both vacuum and electrokinetic injection. Separations are performed at 100 V/cm or 120 V/cm. In all cases, the DNA of interest is detected within 40 minutes. The capillary is flushed with new buffer for two minutes after each run, prior to the next injection.

EXAMPLE 5B

Capillary Electrophoresis by Capillary Gel Electrophoresis

CGE is performed on a Dionex CES1A capillary electrophoresis system (Dionex, Inc., Sunnyvale, Calif.) using reverse polarity. Temperature is ambient and UV absorbance is set at 260 nm. Data collection and analysis are performed on the Dionex A1450 data system.

Primer mediated amplification of nucleic acids is performed as in Examples 1 and/or 2 above. Separations of nucleic acid fragments are performed using μPage3™ (3% C, 3% T) polyacrylamide gel electrophoresis columns, 40 cm effective length, with μPage3™ buffer (J&W Scientific, Folsom, Calif.). Ethidium bromide is added (10 μm) to the buffer immediately before use. Separations are performed at 210 V/cm, with all analytes of interest eluted within 80 minutes.

EXAMPLE 6

DAF on Subgenomic DNA Template

EXAMPLE 6A

DAF on YACs

Several clones from a soybean YAC library were amplified with a mini-hairpin primer GCGAAGC-CTG(SEQ ID NO:4), according to the protocol in Example 1. See FIG. 6. Good fingerprints were obtained from YACs containing between 100 and 300 kb of soybean DNA.

EXAMPLE 6B

DAF on PCR Products

PCR amplifications were done in a total volume of 25 μl containing 0.25 μM of each primer, 0.6 units of AmpliTaq DNA polymerase (Perkin-Elmer/Cetus, Norwalk, Conn.), 200 μM of each deoxyribonucleoside triphosphate (dNTP), 1.5 mM MgCl$_2$, 10 mM KCl, 10 mM Tris·IICl, pH 8.3, and 50–100 ng of template DNA. The mixture was amplified in 35 cycles of 10 sec at 96° C., 10 sec at 60° C., and 2 min at 72° C. in a thermal cycler (TwinBlock, Ericomp, San Diego, Calif.).

Consistent DAF profiles from a 1.1 kb PCR product defining a STS within pUTG-132a, a marker tightly linked to the nts locus in soybean. See FIG. 7. Several DNA polymorphisms were evident and distinguished some of the closely related soybean experimental lines.

EXAMPLE 7

ASAP for Bulked Searegant Analysis (BSA)

BSA was performed on soybean plants to detect a DAF marker for the supernodulation locus (nts) by ASAP analysis. See FIGS. 1A and B. Pools of soybean DNA from wild type, and supernodulating F$_2$ segregants, and controls were amplified with primer an unstructured octamer primer and then re-amplified with mini-hairpin primers or an SSR degenerate primer. Reamplification resulted in polymorphic bands differentiating the bulked DNA.

Using BSA with DAF, markers associated with particular traits or genomic regions can be directly identified using pooled DNA-samples in species for which there is no genetic or molecular map. Individuals in a segregating population that express or fail to express a particular trait are pooled, and amplification fragment length polymorphisms (AFLPs) between the pooled samples become linked to the trait of interest. The fact that these pools are large results in the random assortment of all the genetic variability in the parental material, except for the controlled sorting for the chromosome region linked to the desired phenotype. Thus, this technique, bulked segregant analysis (BSA), can be used to map simple and complex traits with the sole knowledge of phenotype. The approach is applicable both to traits controlled by single genes and those controlled by multiple genes.

EXAMPLE 8

DAF on Plasmid DNA

The DAF procedure, including separation on polyacrylamide gel and silver staining, was performed as described in Example 1 using a decamer mini-hairpin primer HP$_7$-CTG on a DNA template generated from plasmid pUC18. A laser densitometric scan of the silver stained gel was generated. Each lettered peak of the laser scan corresponded to a band which was visible on the silver stained gel. The molecular weights of each band was as follows a) 971, b) 665, c) 568, d) 435, e) 360, f) 312, g) 295, h) 267, i) 257, j) 229, k) 185, l) 139, and m) 103.

Additional information relevant to the present invention can be found in the references listed in the Bibliography, which references are expressly incorporated herein, in their entirety, by reference.

As will be apparent to those skilled in the art, in light of the foregoing disclosure and the disclosure in the parent applications, many modifications, alterations, and substitutions are possible in the practice of this invention without departing from the spirit or scope thereof.

BIBLIOGRAPHY

Ausubel, et al., *Current Protocols in Molecular Biology*, John Wiley & Sons, Inc.

Bassam, B. J., Caetano-Anolles, G. and Gresshoff, P. M. 1992. DNA amplification fingerprinting of bacteria. Appl. Microbiol. Biotechnol. 38:70–76.

Beattie KL, Fowler RF (1991), Solid Phase Gene Assembly. Nature 352:548–549.

Beattie KL, Logsdon JJ, Anderson RS, Espinosa-Lara JM, Maldonado (1988), *Gene Synthesis Technology: Recent Developments and Future Prospects*. Biotechnol. Appl. Biochem. 10:510–521.

Caetano-Anolles, G. and Gresshoff, P. M., "DNA Amplification Fingerprinting of Plant Genomes", *Methods in Molecular and Cellular Biology*, 5:62–70 (1994)

Caetano-Anolles, G. and Gresshoff, P. M., "DNA Amplification Fingerprinting Using Arbitrary Mini-hairpin Oligonucleotide Primers", *Bio/Technology*, 12:619–623 (1994)

Caetano-Anolles, G., Bassam, B. J. and Gresshoff, P. M. 1992. Primer-template interactions during DNA amplification fingerprinting with single arbitrary oligonucleotides. *Mol. Gen. Genet.* 235:157–165.

Caetano-Anolles, G., Bassam, B. J., and Gresshoff, P. M., "DNA Amplification Fingerprinting Using Very Short Arbitrary Oligonucleotide Primers", *Bio/Technology*, 9:553–557 (1991)

Caetano-Anolles, G. and Gresshoff, P. M., "DNA Amplification Fingerprinting: A general Tool with Applications in Breeding, Identification and Phylogenetic Analysis of Plants", *Molecular Ecology and Evolution: Approaches and Applications*, pp. 17–31 (1994)

Caetano-Anolles, G., Bassam, B. J., and Gresshoff, P. M., "DNA Amplification Fingerprinting with Very Short Primers", pp. 18–24

Caetano-Anolles, G., "MAAP: a Versatile and Universal Tool for Genome Analysis", *Plant Mol. Biol.*, 25:1011–1026 (1994)

Caetano-Anolles, G., Bassam, B. J., and Gresshoff, P. M., "Buffer Components Tailor DNA Amplification with Arbitrary Primers", *Cold Spring Harbor Laboratory Press*, 4:59–61 (1994)

Caetano-Anolles, G., "Amplifying DNA with Arbitrary Oligonucleotide Primers", *Cold Spring Harbor Laboratory Press*, 3:1–10 (1993)

Callahan, L. M., Caetano-Anolles, G., Bassam, B. J., Weaver, K., MacKenzie, A., and Gresshoff, P. M., "DNA Fingerprinting of Turfgrass", *Golf Course Management*, June 1993

Dramanac R, Strezoska Z, Labat I, Drmanac S. Crkvenjakov R (1990), *Reliable Hybrization of Oligonucleotides As Short as Six Nucleotides*. DNA and Cell Biology 9:527–534.

Eskew, D. L., Caetano-Anolles, G., Bassam, B. J., and Gresshoff, P. M., "DNA Amplification Fingerprinting for the Azolla-Anabaena Symbiosis", *Plant Mol. Biol.*, 21:363–373 (1993)

Gresshoff, P. M., "Plant Genome Analysis by Single Arbitrary Primer Amplification", Probe, Vol. 4, No. 1/2, pp. 32–36 (July 1993-July 1994)

Lamture JB, Beattie KL, Burke BE, Eggers MD, Ehrlich DJ, Fowler R. Hollis MA, Kosicki BB, Reich RK, Smith SR, Varma RS, Hogan ME (1994), Direct Detection of Nucleic Acid Hybridization on the Surface of a Charge Coupled Device. Nucleic Acids Res. 22:2121–2125.

Landau-Ellis, D., Angermüller, S., Shoemaker, R., and Gresshoff, P. M. 1991. The genetic locus controlling supernodulation in soybean (*Glycine max L.*) co-segregates tightly with a cloned molecular marker. *Mol. Gen. Genet.*, 228:221–226.

Maier E, Crollius HR, Lehrach H (1994), Hybridization Techniques on Gridded High Density DNA and in Situ Colony Filters Based on Fluorescense Detection. Nucleic Acids Res. 22:3423–3424.

Nelson, D. L., Ledbetter, S. A., Corbo, L., Victoria, M. F., Ramirez-Solis, R., Webster, T. D., Ledbetter, D. H., and Caskey, C. T. 1989. Alu polymerase chain reaction: a method for rapid isolation of human-specific sequences from complex DNA sources. *Proc. Natl. Acad. Sci. USA*, 86:6686–6690.

Nikoforov TT, Rendle RB, Goelet P, Rogers Y. Kotewicz ML, Anderson S, Trainer GI, Knapp MR (1994), Genetic Bit Analysis: A Solid Phase Method for Typing Single Nucleotide Polymorphisms. Nucleic Acids Res. 22:4167–4175.

Prabhu, R. R. and Gresshoff, P. M., "Inheritance of Polymorphic Markers Generated by DNA Amplification Fingerprinting and their use as Genetic Markers in Soybean", *Plant Mole. Biol.*, 26:105–116 (1994)

Riley, J., Butler, R., Ogilvie, D., Finniear, R., Jenner, D., Powell, S., Anand, R., Smith, J. C., and Markham, A. F. 1990. A novel rapid method for the isolation of terminal sequences from yeast artificial. chromosome (YAC) clones. *Nucl. Acids Res.* 18:2887–2890.

Sambrook, et al., *Molecular Cloning*, Cold Spring Harbor

Southern EM, Case-Green SC, Elder JK, Johnson M, Mir KU, Wang L, Williams JC (1994), Arrays of Complementary Oligonucleotides for Analysing the Hybridization Behavior of Nucleic Acids. Nucleic Acids Res. 22:1368–1373.

Weaver, K. R., Caetano-Anolles, G., Gresshoff, P. M., and Callahan, L. M., "Isolation and Cloning of DNA Amplification Products from Silver-Stained Polyacrylamide Gels", *BioTechniques*, Vol. 16, No. 2, pp. 226–227 (1994)

What is claimed is:

1. An oligonucleotide construct comprising a structure selected from the group consisting of $(B_x)_n(N)_m$ and $(N)_m(B_x)_n$, wherein B is A, T, G, or C and wherein each B may be the same as or different than any other B in the construct so long as at least one B differs from another B, x is a whole number from 2 to 5, n is a whole number from 2 to 10, N is a degenerate base, and m is a whole number from 1 to 10.

2. The construct of claim 1 wherein n is 3 to 6.

3. The construct of claim 1 wherein m is 2 to 5.

4. The construct of claim 3 wherein m is 2 or 3.

5. The construct of claim 1 which further comprises an arbitrary sequence having the formula $(R)_y$, wherein R is selected from the group consisting of C, G, T, and A, and y is a whole number from 1 to 25, and which arbitrary sequence $(R)_y$ is connected to $(B_x)_n$, $(N)_m$, or both $(B_x)_n$ and $(N)_m$, or is within $(B_x)_n$ or $(N)_m$.

6. The construct of claim 5 wherein y is 2 to 10.

7. An oligonucleotide mini-hairpin primer having a 3' single stranded end and a 5' end which primer comprises a double stranded stem of at least 2 complementary annealed base pairs, the double stranded stem extending to the 5' end of the primer and the other end of the stem extending as the single strand of at least 3 bases to the 3' end of the primer, and intermediate to the 5' and 3' ends of the stem, a single stranded loop of at least 3 bases.

8. The primer of claim 7 wherein the loop consists of 3 or 4 bases.

9. The primer of claim 7 wherein the stem consists of 2 base pairs.

10. The primer of claim 7 wherein the base pairs are only GC base pairs.

11. The primer of claim 7 wherein the single strand consists of 3 to 8 bases.

12. An oligonucleotide primer having a 3' single stranded end and a 5' end which primer comprises a double stranded stem of 2 complementary annealed base pairs, the double stranded stem extending to the 5' end of the primer and the other end of the stem extending as the single strand of at least 3 bases to the 3' end of the primer, and intermediate to the 5' and 3' ends of the stem, a single stranded loop of 3 or 4 bases.

13. The oligonucleotide primer of claim 12 wherein the loop has 3 bases.

14. The oligonucleotide primer of claim 12 wherein the loop has 4 bases.

15. The oligonucleotide primer of claim 12 wherein one of the bases of the loop is A.

16. The oligonucleotide primer of claim 12 wherein the length of the single strand is of 3 to 8 nucleotides.

17. The oligonucleotide primer of claim 12 which is a deoxyribonucleotide sequence.

18. The oligonucleotide primer of claim 12 which is a ribonucleotide sequence.

19. The oligonucleotide primer of claim 12 wherein the double stranded stem has two complementary GC pairs.

20. The oligonucleotide primer of claim 13 wherein the nucleotides of the loop are GAA or GTT.

21. The oligonucleotide primer of claim 18 wherein the nucleotides of the loop are GAAA.

22. The oligonucleotide primer of claim 14 which is a DNA primer, and wherein the loop comprises a nucleotide sequence selected from the group consisting of GAA, GTTA, and GNAA, wherein N is A, G, C, and T.

23. The oligonucleotide primer of claim 22 wherein the loop comprises the nucleotide sequence GNAA, wherein N is G, A, C, and T.

24. The oligonucleotide primer of claim 13 wherein the single strand comprises a sequence of nucleotides selected from the group consisting of CTG, GCTG, NCTG, GAGCTG, NAGCTG, and CCGAGCTG, wherein N is A, G, C, and T.

25. The oligonucleotide primer of claim 24 wherein N is G.

26. The oligonucleotide primer of claim 14 wherein the single strand has a sequence selected from the group consisting of GCTG and GAGCTG.

27. The oligonucleotide primer of claim 12 wherein the primer has an extended 5' end.

28. The oligonucleotide primer of claim 12 wherein the primer has a sequence selected from the group consisting of GCGAAGCGCTG, GCGAAGCGAGCTG, and GCGAAGCCCGAGCTG.

29. The oligonucleotide primer of claim 12 wherein one or more nucleotides at the 3' or 5' end of the primer has been replaced by a base selected from the group consisting of hypoxanthine, 6H,8H03,4-dihydropyrimido(4,5-c) (1,2) oxazin-7-one, and 2-amino-6-methoxyaminopurine.

30. A combination of a multiplicity of the oligonucleotide primers of claim 12, wherein the 3' single stranded end extending from the double stranded stem comprises 3 nucleotides, wherein the nucleotides constitute combinations of the known 4 bases of DNA, and wherein the portion of the oligonucleotide primers other than the 3' single stranded end extending from the double stranded stem contain identical sequences in each of the primers.

31. An oligonucleotide primer having a 3' single stranded end and a 5' end which primer comprises a double stranded stem of at least 2 complementary annealed base pairs, the double stranded stem extending to the 5' end of the primer and the other end of the stem extending as the single strand of at least 3 bases to the 3' end of the primer, and intermediate to the 5' and 3' ends of the stem, a single stranded loop.

32. The primer of claim 12 which is annealed to a DNA template.

33. The primer of claim 12 wherein the first three bases of the 3' end are determinative to produce reproducible fingerprints.

34. The primer of claim 33 wherein the three bases at the 3' end of the primer are arbitrary.

35. The oligonucleotide primer of claim 31 wherein the loop has 3 or 4 bases, wherein at least one of the bases is A.

36. An oligonucleotide primer having a 3' single stranded end and a 5' end which primer comprises a double stranded stem of at least 2 complementary annealed base pairs, the double stranded stem extending to the 5' end of the primer and the other end of the stem extending as the single strand of at least 3 bases to the 3' end of the primer, and intermediate to the 5' and 3' ends of the stem, a single stranded loop.

37. The primer of claim 36 wherein the first three bases of the 3' end are determinative to produce reproducible fingerprints.

38. The primer of claim 37 wherein the three bases at the 3' end of the primer are arbitrary.

39. The oligonucleotide primer of claim 36 wherein the loop has 3 or 4 bases, wherein at least one of the bases is A.

* * * * *

UNITED STATES PATENT AND TRADEMARK OFFICE
CERTIFICATE OF CORRECTION

PATENT : 5,962,221
DATED : October 5, 1999
INVENTOR(S) : Gustavo Caetano-Anollés

It is certified that error appears in the above-identified patent and that said Letters Patent is hereby corrected as shown below:

On the title page:
    [76] should read as follows:
        --[75] Gustavo Caetano-Anollés, Knoxville, Tenn.--;

Add [73] as follows:
        --[73] Assignee: The University of Tennessee Research Corporation, Knoxville, Tenn.--; and Add the Attorney, Agent or Firm as follows:
        --Attorney, Agent or Firm--Weiser & Associates, P.C.--.

Signed and Sealed this

Tenth Day of October, 2000

*Attest:*

Q. TODD DICKINSON

*Attesting Officer*      *Director of Patents and Trademarks*